United States Patent
Javaheri

(10) Patent No.: US 11,790,317 B2
(45) Date of Patent: Oct. 17, 2023

(54) SYSTEM, DEVICE, AND PROCESS FOR TRACKING PRODUCT

(71) Applicant: GOLDEN STATE FOODS CORP., Irvine, CA (US)

(72) Inventor: Guilda Javaheri, Irvine, CA (US)

(73) Assignee: GOLDEN STATE FOODS CORP., Irvine, CA (US)

(*) Notice: Subject to any disclaimer, the term of this patent is extended or adjusted under 35 U.S.C. 154(b) by 603 days.

(21) Appl. No.: 16/704,314

(22) Filed: Dec. 5, 2019

(65) Prior Publication Data
US 2020/0184416 A1 Jun. 11, 2020

Related U.S. Application Data

(60) Provisional application No. 62/776,149, filed on Dec. 6, 2018.

(51) Int. Cl.
| | |
|---|---|
| *G06Q 10/0875* | (2023.01) |
| *G06Q 10/0833* | (2023.01) |
| *G01N 33/02* | (2006.01) |
| *G06K 7/14* | (2006.01) |
| *G06Q 10/083* | (2023.01) |

(52) U.S. Cl.
CPC ......... *G06Q 10/0875* (2013.01); *G01N 33/02* (2013.01); *G06K 7/1417* (2013.01); *G06K 7/1443* (2013.01); *G06Q 10/0833* (2013.01); *G06Q 10/0838* (2013.01)

(58) Field of Classification Search
CPC . H04L 9/0637; H04L 67/1042; H04L 9/3238; H04L 9/50; G06Q 10/087; G06Q 30/04

USPC ........................................................ 340/10.1
See application file for complete search history.

(56) References Cited

U.S. PATENT DOCUMENTS

| | | | | |
|---|---|---|---|---|
| 2013/0162407 | A1* | 6/2013 | Moore | G08B 13/2462 340/10.1 |
| 2016/0379298 | A1* | 12/2016 | Isaacson | G06Q 30/0633 705/26.62 |
| 2017/0262973 | A1* | 9/2017 | Johnston | G06T 7/13 |
| 2018/0096175 | A1 | 4/2018 | Schmeling et al. | |

(Continued)

OTHER PUBLICATIONS

International Search Report and Written Opinion issued in PCT/US2019/064643, dated Feb. 6, 2020.

(Continued)

*Primary Examiner* — Olusegun Goyea
(74) *Attorney, Agent, or Firm* — BakerHostetler

(57) ABSTRACT

A system configured to track, trace and monitor product. In some aspects, the system is configured to track product and capture product related information and includes a network interface configured to receive product related information over a network from a plurality of tracking devices located at a plurality of facilities. The system also includes a database configured to store the product related information from the plurality of tracking devices located at the plurality of facilities. The system also includes a processor configured to be responsive to and control at least the database and the network interface. The system also includes the processor and the database being further configured to implement blockchain technology with respect to the product related information to generate a blockchain ledger of the product related information.

15 Claims, 12 Drawing Sheets

(56) References Cited

U.S. PATENT DOCUMENTS

| | | | | |
|---|---|---|---|---|
| 2018/0276614 A1* | 9/2018 | Blair | .................... | G08G 1/141 |
| 2018/0284093 A1* | 10/2018 | Brown | .................... | H04W 4/38 |
| 2018/0285810 A1* | 10/2018 | Ramachandran | .... | G06Q 10/087 |
| 2018/0336515 A1* | 11/2018 | Mehring | ............... | H04L 9/0637 |
| 2019/0122322 A1* | 4/2019 | Perez | .................... | G06F 16/23 |
| 2019/0236527 A1* | 8/2019 | Bhaumik | ............. | G06Q 10/087 |
| 2019/0342085 A1* | 11/2019 | Kube | .................... | H04L 9/3239 |
| 2022/0058578 A1* | 2/2022 | Javaheri | ............... | G06K 7/1443 |

OTHER PUBLICATIONS

International Patent Application No. PCT/US2019/064643; Int'l Preliminary Report on Patentability; dated Jun. 17, 2021; 10 pages.

\* cited by examiner

SYSTEM, DEVICE, AND PROCESS FOR TRACKING PRODUCT

CROSS-REFERENCE TO RELATED APPLICATIONS

This application claims the benefit of U.S. Provisional Application No. 62/776,149 filed on Dec. 6, 2018, which is hereby incorporated by reference in its entirety for all purposes as if fully set forth herein.

BACKGROUND OF THE DISCLOSURE

1. Field of the Disclosure

This disclosure is directed to a system, device, and process for tracking product. More particularly, the disclosure is directed to a system, device, and process for tracking product through one or more facilities. More particularly, the disclosure is directed to a system, device, and process for tracking product through one or more facilities and capturing product related information. Additionally, the disclosure is directed to a system, device, and process for tracking product through one or more facilities and capturing product and ambient related information. Moreover, the disclosure is directed to a system, device, and process for tracking product through one or more facilities and capturing inventory information for each participating entity in a supply chain. Additionally, the disclosure is directed to a system, device, and process for tracking product through one or more facilities and applying algorithms, aggregating information, configuring exception-based alerts, and using artificial intelligence or machine learning to provide insights as product moves, is added, consumed, or transacted throughout the entirety of the product lifecycle.

2. Related Art

A number of approaches have been taken recently to track product from a source to a final destination in order to be able to obtain information regarding the product. However, these conventional approaches lack detailed information necessary for understanding possible issues related to the product.

For example, in the food industry, the various facilities and entities in a food supply chain typically only keep physical records that are limited to where the particular food product was received and where a particular food product is shipped. This limited information may exist in different locations and formats. Moreover, access to this limited information may be difficult and time-consuming.

Accordingly, it would be highly beneficial to obtain detailed information on a product from its source to a final destination. Additionally, it would be highly beneficial to obtain detailed information on a product from its source to a final destination from a single platform having a greater level of accuracy. Moreover, it would be highly beneficial to obtain detailed information on a product from its source to a final destination having a greater speed of access to the information. Furthermore, it would be highly beneficial to obtain information on a product lifecycle from a permissioned based visualization or dashboard where artificial intelligence or machine learning applies algorithms, business rules, or consensus mechanisms to the data and calculates exceptions providing insights through a persona-based management system.

SUMMARY OF THE DISCLOSURE

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by a data processing apparatus, cause the apparatus to perform the actions. One general aspect includes a system configured to track product and capture product related information including: a network interface configured to receive product related information over a network from a plurality of tracking devices located at a plurality of facilities. The system also includes a database configured to store the product related information from the plurality of tracking devices located at the plurality of facilities. The system also includes a processor configured to be responsive to and control at least the database and the network interface. The system also includes the processor and the database being further configured to implement blockchain technology with respect to the product related information to generate a blockchain ledger of the product related information, where the product related information includes a location of the product, an identification of the product, and at least one of the following: a temperature of the product and a temperature of an environment of the product; where the product related information may further include quantity, unit of measure, shelf life information, as well as any other inventory management data; the product related information may be in a format compliant to industry standards such as GS1; the product related information not specifically read off the tag or otherwise captured may be transmitted to the system through an Application Program Interface (API); and where the identification of the product is based in part on a machine readable code located with the product, the machine readable code including the identification of the product and the machine readable code being implemented with at least one of the following: a radio frequency identification (RFID) device, a barcode, a QR (quick response) code, and a data matrix (DM) code. In other aspects, information that is not specifically included in a product identifier may be sent through an Application Program Interface (API) or other interfaces and product information may be derived through associations and references to chain the data from one or more entities in the supply chain. Other aspects include corresponding computer systems, apparatus, and computer programs recorded on one or more computer storage devices, each configured to perform the actions of the methods.

Implementations may include one or more of the following features. The system where: the processor is further configured to receive an information request for the product. The system may also include the processor further configured to analyze the database including the blockchain ledger to determine requested information in response to the information request for the product. The system may also include the processor further configured to transmit the requested information to a computer. The system may also include where the requested information includes information on a particular one of the product, a particular one of the facilities, a case number of the product, a lot number of the product, a batch number of the product, a quantity, a unit of measure, and an item number of the product; and where the information request includes at least one of the following: a tracking request and a traceability request. The system where: the processor is further configured to receive an inventory request for the product. The system may also include the processor further configured to analyze the database including the blockchain ledger to determine inventory information in response to the inventory request for the product. The system may also include the processor further configured to transmit the inventory information to a computer, where the inventory information includes at least one of the following: an inventory determination, a replacement determination, a supply chain determination, consumption metrics, inventory counts, a gross inventory, a remaining shelf life determination, and a forecasted inventory. The system where: the product related information further includes an image captured by a camera device implemented by one of the plurality of tracking devices. The product related information further includes the image captured by the camera device implemented by one of the plurality of tracking devices. The system where: the processor is further configured to analyze the image captured by the camera device implemented by one of the plurality of tracking devices to determine at least one of the following: degradation of product, quality characteristics, volume, or quantity on hand. The processor may be configured to receive and analyze smart shelf signals for on hand inventory management or volume. In certain aspects, computer vision may be implemented to determine inventory, such as case counts on a shelf on "hard to read" items, determine "product availability" on shelf for bulk products, and the like. The system further including the plurality of tracking devices, each of the plurality of tracking devices including: a machine readable code reader configured to read a machine readable code located with a product, the machine readable code including an identification of the product and the machine readable code being implemented with at least one of the following: a radio frequency identification (RFID) device, a barcode, a QR (quick response) code, and a data matrix (DM) code. In one or more aspects, the system may utilize smart boxes. In this regard, a smart box may include corrugate imbedded tracking devices. For example, a smart box may embed an identifier into the corrugate (box) through (conductive) ink and embedding code in the corrugate. In one or more aspects, data may also be ingested through Application Program Interfaces (APIs) and other interfaces to legacy systems. In this regard, data from the radio frequency identification (RFID) device or tag may be chained in a blockchain with data from other interfaces. The system may also include at least one sensor configured to sense a physical characteristic of the product including at least one of the following: a temperature of the product and a temperature of an environment of the product. The system may also include a detection unit configured to receive the information from the sensor. The system may also include a device processor configured to implement and control the detection unit and the machine-readable code reader; and a transceiver configured to transmit product related information over the network to the processor, the product related information including the location of the product, quantity of the product, the identification of the product, and at least one of the following: the temperature of the product, remaining shelf life of the product, and the temperature of an environment of the product. In further aspects, the product related information may include additional product information such as non-GMO (non-genetically modified organism), antibiotics, organic, grass fed, certifications, and other sustainability related information to be captured and chained in the blockchain as part of possible genealogy queries. Implementations of the described techniques may include hardware, a method or process, or computer software on a computer-accessible medium.

One general aspect includes a device configured to track product and capture product related information including: a machine readable code reader configured to read a machine readable code located with a product, the machine readable code including an identification of the product and the machine readable code being implemented with at least one of the following: a radio frequency identification (RFID) device, a barcode, a QR (quick response) code, and a data matrix (DM) code. The device also includes at least one sensor configured to sense a physical characteristic of the product including at least one of the following: a temperature of the product, a remaining shelf life of the product, and a temperature of an environment of the product. The device also includes a detection unit configured to receive the information from the sensor. The device also includes a processor configured to implement and control the detection unit and the machine-readable code reader; and a transceiver configured to transmit product related information over a network to a data collection system, the product related information including a location of the product, the identification of the product, and at least one of the following: the temperature of the product and the temperature of an environment of the product. Other aspects may include systems, devices, and processes utilizing, obtaining, and/or determining remaining shelf life information, process orchestration business rules, product characteristics, and the like. Other aspects include corresponding computer systems, apparatus, and computer programs recorded on one or more computer storage devices, each configured to perform the actions of the methods.

Implementations may include one or more of the following features. The device where: the machine-readable code reader includes a radio frequency identification reader device. The device may also include the machine-readable code that includes the radio frequency identification device. The device further including: a plurality of radio frequency antennas connected to the machine-readable code reader, the plurality of the radio frequency antennas arranged in different locations of a facility. The device may also include the plurality of the radio frequency antennas configured to receive the identification of the product in different locations of the facility. The device may also include a plurality of sensors. The device may also include where the detection unit is further configured to receive information from the plurality of sensors. The device further including: a camera device configured to capture an image of at least one of the following: the product, an environment where the product is located, and the machine-readable code. In one aspect, the camera device may be implemented with computer vision functionality or a computer vision device may be utilized. In this regard, the computer vision functionality may be used to determine on hand quantity on a shelf and the like. In further aspects, "smart shelves" may be implemented and configured to calculate on hand quantity based on weight on shelf for missed reads, automate inventory validation (physical inventory), and the like. The device may also include where the product related information further includes the image captured by the camera device. The device may also include where the transceiver is configured to transmit over the network the product related information to the data collection system that includes the image captured by the camera device. Implementations of the described techniques may include hardware, a method or process, or computer software on a computer-accessible medium.

One general aspect includes a process of operating a system configured to track product and capture product related information including: receiving product related information over a network with a network interface from a plurality of tracking devices located at a plurality of facilities. The process may include obtaining information from a plurality of interface (API) calls and chaining the data through associations, references, or other data not explicitly placed on the tracking device such as a tag. In one aspect, the process may include aspects to ingest data from silo legacy systems and associate it in the blockchain to establish a genealogy and provenance of the product throughout its life cycle. The process also includes storing the product related information in a database from the plurality of tracking devices located at the plurality of facilities. The process also includes responding to and controlling at least the database and the network interface with a processor. The process also includes implementing blockchain technology with respect to the product related information and generating a blockchain ledger of the product related information with the processor and the database, where the product related information includes a location of the product, an identification of the product, remaining shelf life of the product, quantity of the product, maintaining provenance of the product, and at least one of the following: a temperature of the product and a temperature of an environment of the product; and where the identification of the product is based in part on a machine readable code located with the product, the machine readable code including the identification of the product and the machine readable code being implemented with at least one of the following: a radio frequency identification (RFID) device, a barcode, a QR (quick response) code, and a data matrix (DM) code. In one or more aspects, the system may utilize smart boxes. In this regard, a smart box may include corrugate imbedded tracking devices. For example, a smart box may embed an identifier into the corrugate (box) through (conductive) ink and embedding code in the corrugate. Other aspects include corresponding computer systems, apparatus, and computer programs recorded on one or more computer storage devices, each configured to perform the actions of the methods.

Implementations may include one or more of the following features. The process where: receiving an information request for the product with the processor. The process may also include analyzing the database including the blockchain ledger and determining requested information in response to the information request for the product with the processor. The process may also include transmitting the requested information to a computer with the processor. The process may also include where the requested information includes information on a particular one of the product, a particular one of the facilities, a case number of the product, a lot number of the product, a batch number of the product, and an item number of the product; and where the information request includes at least one of the following: a tracking request and a traceability request. The process may also include aspects for determining and/or utilizing characteristics establishing a genealogy or a provenance of the product, information to perform calculations related to product quality, safety, dynamic shelf life, and the like, algorithms configured to execute business rules and send messages if the product falls out of acceptable threshold, and the like. The process may also include aspects for determining and/or utilizing the remaining shelf life of the product. The process where: receiving an inventory request for the product with the processor. The process may also include analyzing the database including the blockchain ledger and determining inventory information in response to the inventory request for the product with the processor. The process may also include transmitting the inventory information to a computer with the processor, where the inventory information includes at least one of the following: an inventory determination, a replacement determination, a supply chain determination, consumption metrics, inventory counts, a gross inventory, remaining shelf life, a product quality determination, a product authenticity determination, a product genealogy determination, a product key characteristics determination (organic, non-GMO, etc.) and a forecasted inventory. The process where: the product related information further includes an image captured by a camera device implemented by one of the plurality of tracking devices. The process where the product related information further includes the image captured by the camera device implemented by one of the plurality of tracking devices. The process where: the processor is further configured to analyze the image captured by the camera device implemented by one of the plurality of tracking devices to determine whether the product has indications of at least one of the following: product quality deterioration, visible product defects (e.g., color, shape, and the like), foreign materials detection, and the like. The process further including implementing the plurality of tracking devices, the process further including: reading a machine-readable code located with a product with a machine-readable code reader, the machine-readable code including an identification of the product and the machine-readable code being implemented with at least one of the following: a radio frequency identification (RFID) device, a barcode, a QR (quick response) code, and a data matrix (DM) code. The process may include sensing a physical characteristic of the product with at least one sensor including at least one of the following: a temperature of the product and a temperature of an environment of the product. The process may also include receiving the information from the sensor with a detection unit. The process may also include implementing and controlling the detection unit and the machine-readable code reader with a device processor; and transmitting product related information over a network to the processor with a transceiver, the product related information including a location of the product, the identification of the product, remaining shelf life of the product, and at least one of the following: the temperature of the product and the temperature of an environment of the product. Implementations of the described techniques may include hardware, a method or process, or computer software on a computer-accessible medium.

One general aspect includes a process of operating a device configured to track product and capture product related information including: reading a machine readable code located with a product with a machine readable code reader, the machine readable code including an identification of the product and the machine readable code being implemented with at least one of the following: a radio frequency identification (RFID) device, a barcode, a QR (quick response) code, and a data matrix (DM) code. The process including sensing a physical characteristic of the product with at least one sensor including at least one of the following: a temperature of the product and a temperature of an environment of the product. The process also includes receiving the information from the sensor with a detection unit. The process also includes implementing and controlling the detection unit and the machine-readable code reader with a processor; and transmitting product related information over a network to a data collection system with a transceiver, the product related information including a location of the product, the identification of the product, and at least one of the following: the temperature of the product and the temperature of an environment of the product. Other aspects include corresponding computer systems, apparatus, and computer programs recorded on one or more computer storage devices, each configured to perform the actions of the methods. In various aspects of the disclosure, it should be noted that the systems, devices, and processes may be associated with one or more mobile or portable devices allowing users to display and/or render data utilizing the one or more mobile or portable devices.

Implementations may include one or more of the following features. The process where: the machine-readable code reader includes a radio frequency identification reader device. The process may also include the machine-readable code includes the radio frequency identification device. The process further including: a plurality of radio frequency antennas connected to the machine-readable code reader, the plurality of the radio frequency antennas arranged in different locations of a facility. The process may also include the plurality of the radio frequency antennas configured to receive the identification of the product in different locations of the facility. The process may also include where the sensor includes a plurality of sensors. The process may also include where the detection unit is further configured to receive information from the plurality of sensors. The process further including: a camera device configured to capture an image of at least one of the following: the product, an environment where the product is located, and the machine-readable code. The process may also include where the product related information further includes the image captured by the camera device. The process may also include where the transceiver is configured to transmit over the network the product related information to the data collection system that includes the image captured by the camera device. Implementations of the described techniques may include hardware, a method or process, or computer software on a computer-accessible medium.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE DISCLOSURE

Figure 1A:
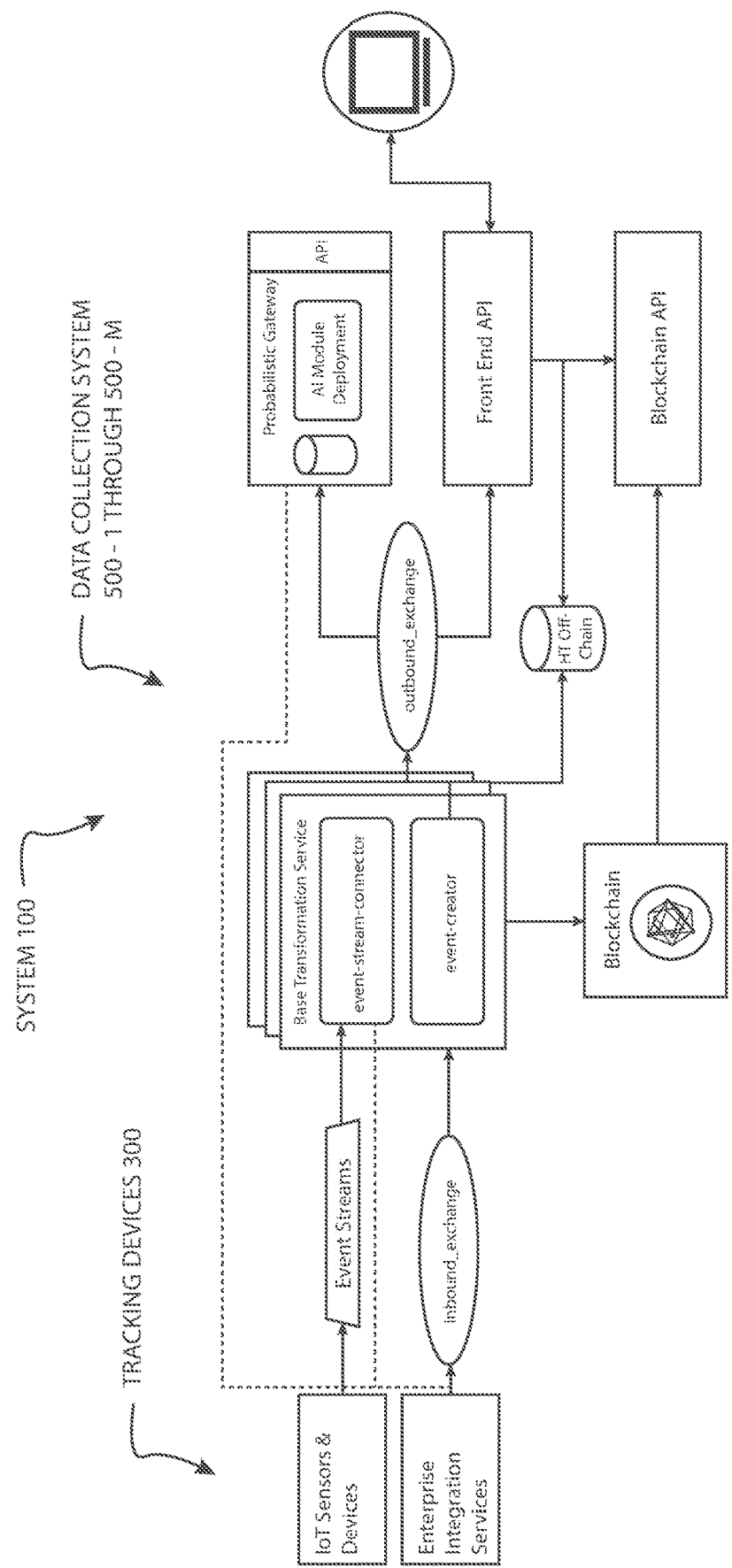
FIG. 1A, FIG. 1B, FIG. 1C, FIG. 1D, and FIG. 1E illustrate a system according to the principles of the disclosure.
Figure 1B:
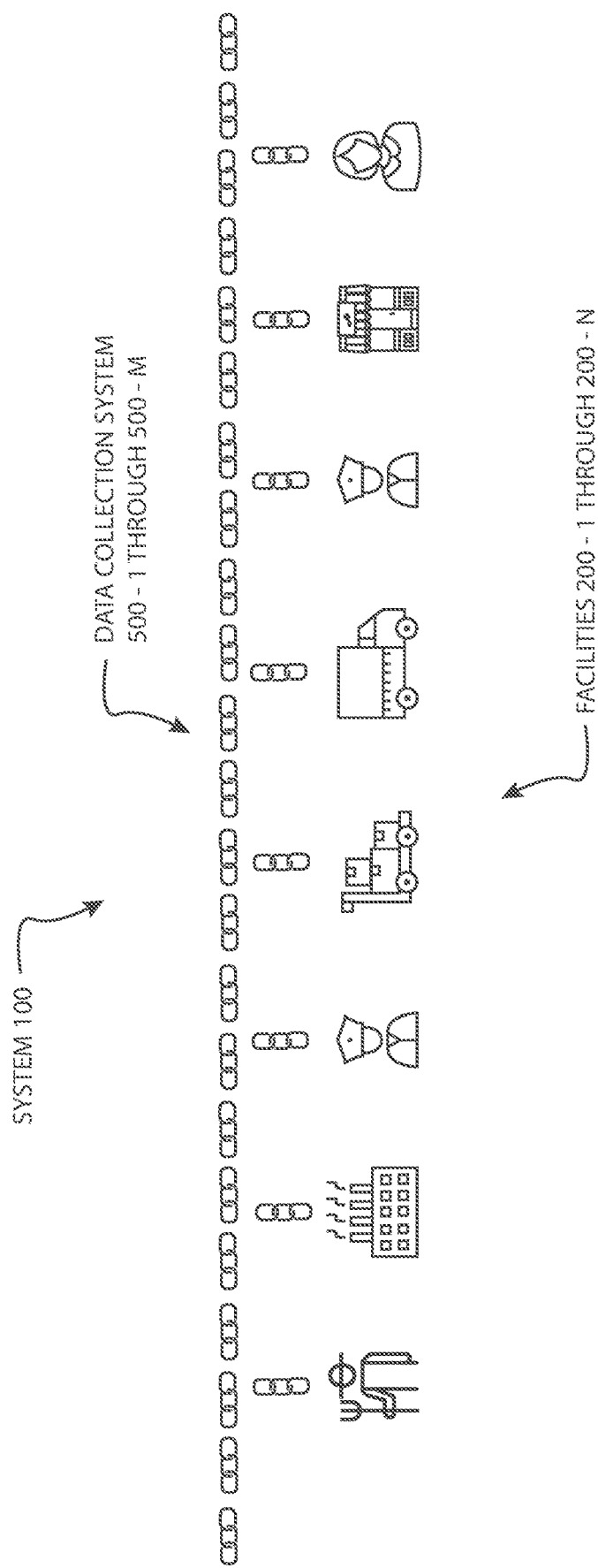
Figure 1C:
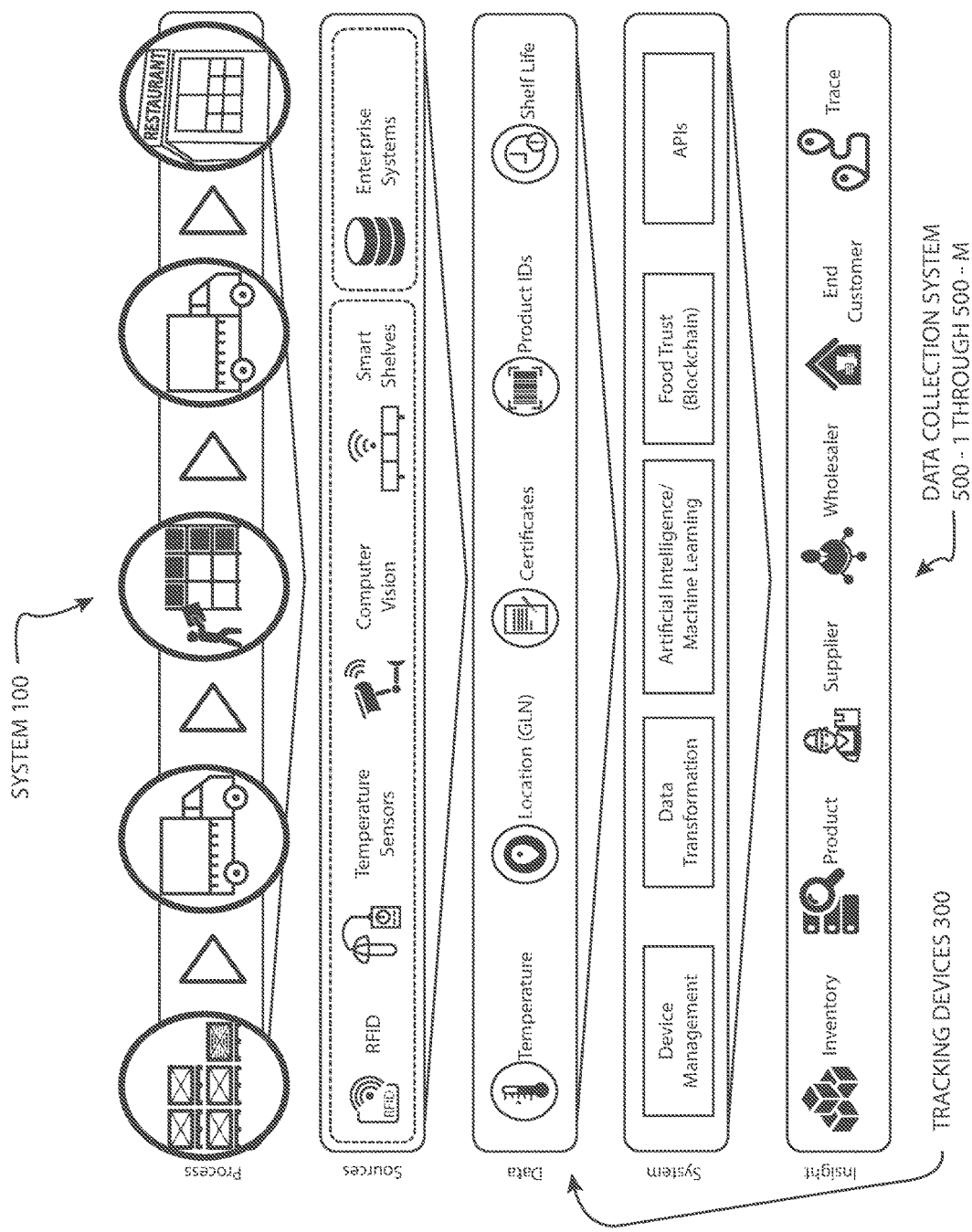
Figure 1D:
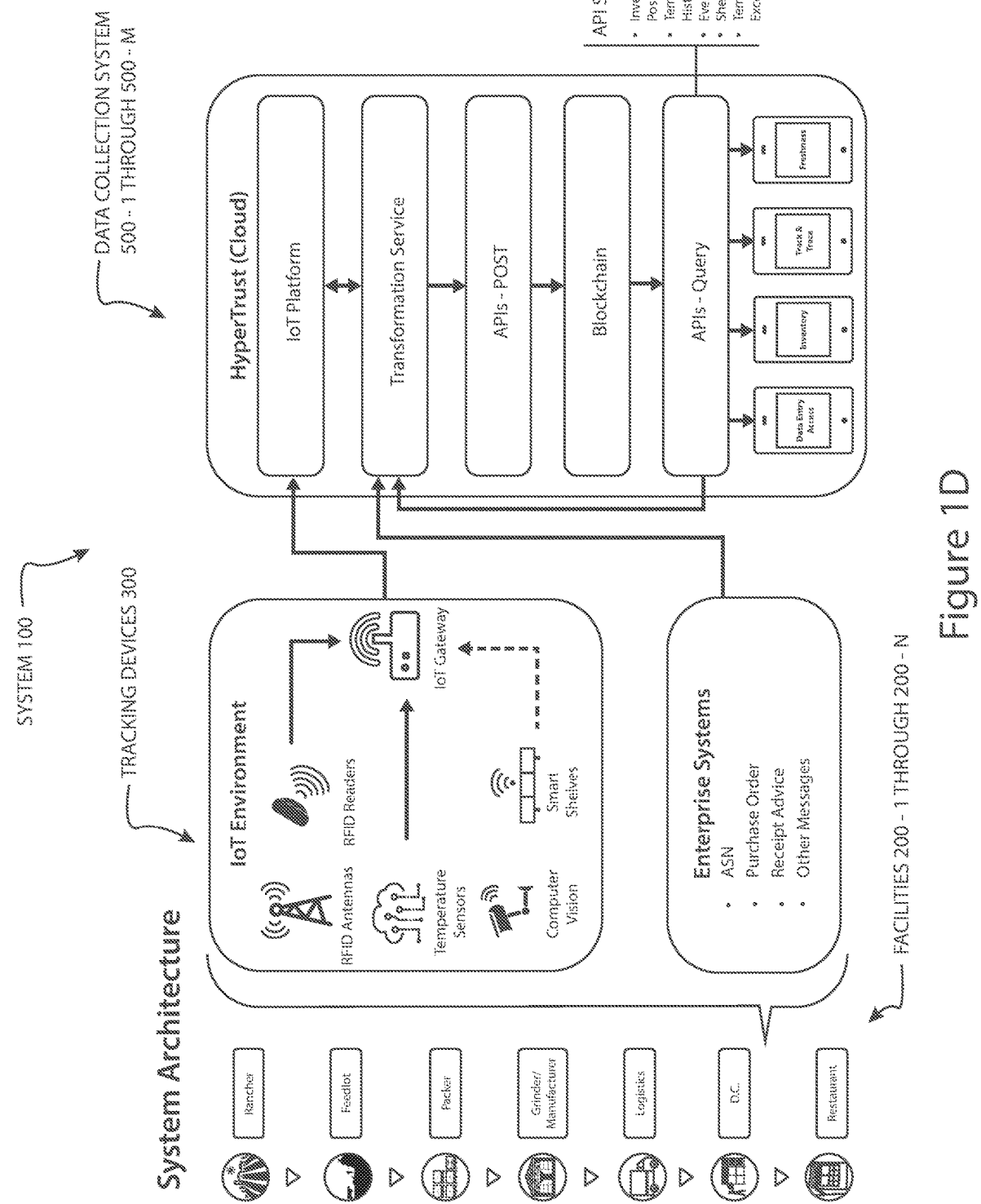
Figure 1E:
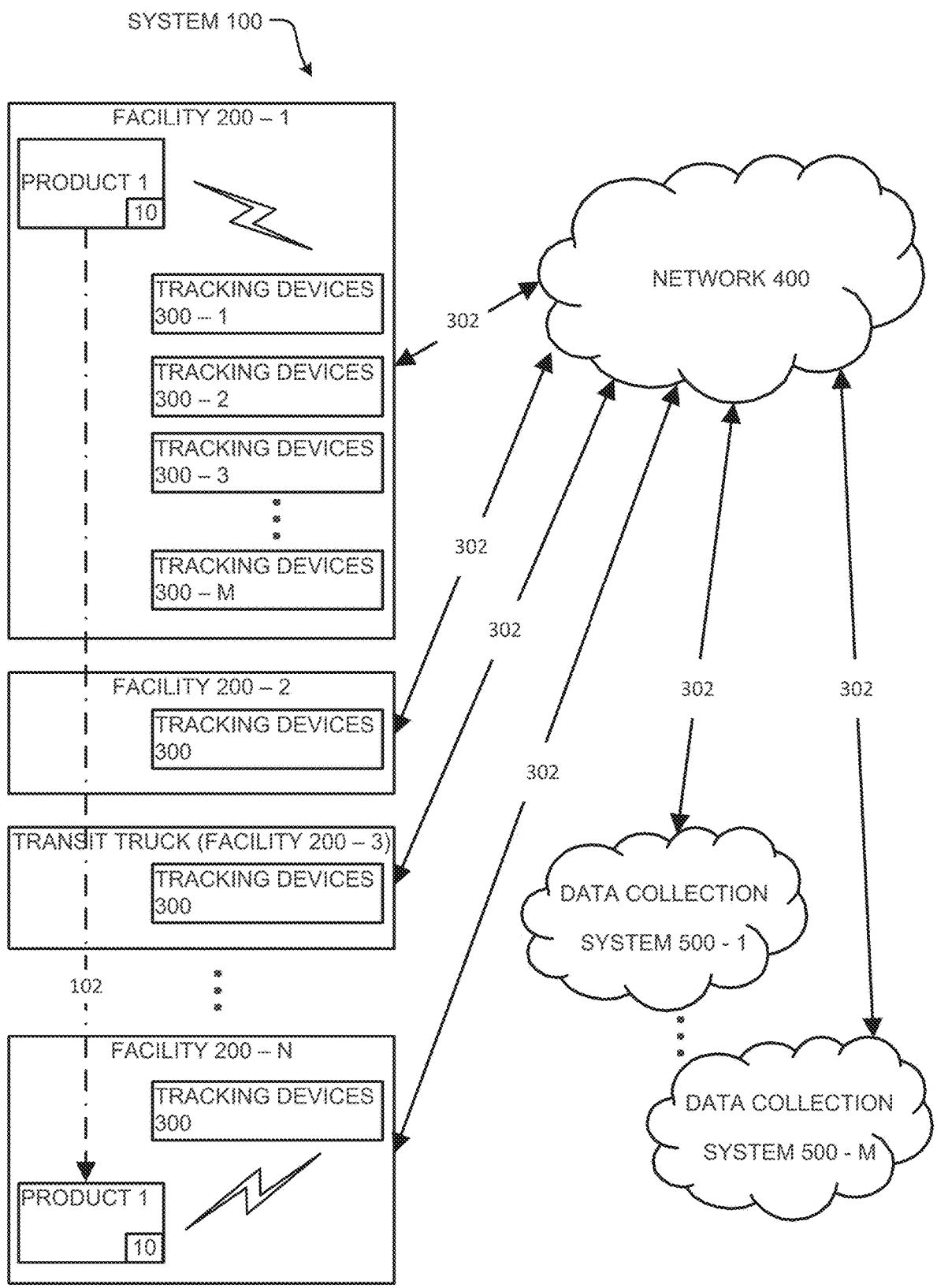

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

FIG. 1A, FIG. 1B, FIG. 1C, FIG. 1D, and FIG. 1E illustrate F a system according to the principles of the disclosure.

In particular, FIG. 1A, FIG. 1B, FIG. 1C, FIG. 1D, and FIG. 1E illustrate a system 100 that may be configured to track a product 1 through at least one facility 200 with at least one tracking device 300. The at least one tracking device 300 may be configured to capture and/or generate product related information 302 of the product 1 and transmit the product related information 302 of the product 1 over a network 400 to a data collection system 500. The data collection system 500 may be configured to receive and store the product related information 302 of the product 1 from the network 400. In one aspect, the network 400 may be the Internet. The data collection system 500 may be further configured to analyze the product related information 302 and generate tracking information, traceability information, inventory information, issues with the product, and/or the like.

In this regard, in some aspects the product 1 may be a plurality of products. In particular, the product 1 may be different products, a plurality of the same products, and/or the like. Additionally, the product 1 may be associated with an identifier 10 that identifies the product 1 in association with one or more of a stock keeping unit (SKU), a Universal Product Code (UPC), a lot of a product, a batch of a product, a pallet of the product, a case of a product, a single unit of the product, and/or the like. In one aspect, the identifier 10 may be a machine-readable identifier that may include a radiofrequency identification (RFID) device, a barcode, a QR code, a Data Matrix (DM) code, and/or the like. In one aspect, the identifier 10 may be an alphanumeric code that may be manually input to the tracking device 300.

In one aspect, the system 100 may track the product 1 in whatever form upon arrival at the facility 200. In this regard, the system 100 may collect the product related information 302 on the product 1 as it arrives at the facility 200. The system 100 may further collect the product related information 302 on the product 1 while it is at the facility 200. The facility 200 may process the product 1. For example, processing of the product 1 may be defined as including one or more of modifying the product, accumulating a plurality of products, disseminating the product, consuming the product, selling the product, disposing of the product, and/or the like. The system 100 may further collect the product related information 302 on the product 1 while it is processed at the facility 200. Finally, the system 100 may collect the product related information 302 on the product 1 as it departs the facility 200 including consumption information if appropriate. In one aspect, the tracking device 300 may obtain the product related information 302 on the product 1 during one or more steps through the facility 200, at every step through the facility 200, periodically as the product 1 moves through the facility 200, at predefined time periods and/or process steps while in the facility 200, while in transit (transportation processes & logistic processes) and the like.

The facility 200 may be any type of facility receiving the product 1, processing the product 1, consuming the product 1, delivering the product 1, transferring the product 1, and/or the like. As further shown in FIG. 1, the facility 200 may include a plurality of facilities 200 (facility 200-1, facility 200-2, facility 200-3, ... facility 200-N; where N is any whole number). In one aspect, each facility 200 may be part of system of organizations, companies, people, activities, transportation, resources, processors, and the like involved in receiving, processing, delivering, and the like the product 1 from a source to customer. In one aspect, a facility 200 may be a service provider and may or may not provide any particular processing, consuming, delivering, or transferring of product. For example, service providers may include data aggregators that may provide data inputs on supply and demand. For example, IoT service providers, data aggregators, third party purchasing organizations, and the like. The facility 200 may involve the transformation and/or delivery of resources, raw materials, components, and the like into a finished and/or intermediate product that is delivered to a next facility 200 or delivered to an end customer.

In one aspect, the system 100 may track the product 1 as it moves through each of the facilities 200 consistent with the above as shown by a dashed arrow 102 extending from the facility 200-1 through facility 200-N. In other words, the system 100 may track the product 1 through its entire product lifecycle, which is illustrated by the dashed arrow 102.

The at least one tracking device 300 may track the product 1 through the facility 200. As further shown in FIG. 1, the tracking device 300 may include a plurality tracking device 300 (tracking device 300-1, tracking device 300-2, tracking device 300-3, ... tracking device 300-M; where M is any whole number). The at least one tracking device 300 may collect the product related information 302 directly or indirectly regarding the product 1 and forward the product related information 302 over a network 400 to the data collection system 500. The at least one tracking device 300 and/or any other component of the disclosure may be implemented as portable or mobile devices. The at least one tracking device 300 may connect directly to the network 400 or indirectly through one or more associated devices or networks to the network 400 over a communication channel as defined herein. The network 400 may further transfer the product related information 302 from the at least one tracking device 300 over a communication channel as defined herein to the data collection system 500. The transfer of the product related information 302 from the tracking device 300, over the network 400 to the data collection system 500 may utilize any known data transmission protocol include one or more of data packets, data frames, text message, MMS, datagram, email, and/or the like. In one or more aspects, the network 400 may include, implement, utilize, and the like blockchain technology and functionality, API technology and functionality, other micro service technology and functionality, and the like. In one or more aspects, the data collection system 500 may be implemented as multiple database replications for each entity. In this regard, the databases 504 may include 1 to M databases (504-1 through 504-M) indicating application of the blockchain architecture utilizing replicated shared ledgers; and the data collection system 500 may include 1 to M systems (500-1 through 500-M).

The data collection system 500 thereafter may store the product related information 302 received from the at least one tracking device 300. The product related information 302 may be obtained from the data collection system 500 by authorized users as needed in order to obtain the information on the product 1. For example, information on the product 1 related to tracking information, traceability information, inventory information, remaining shelf life information, genealogy information, provenance information, issues with the product, and the like.

Product Definition

In one aspect, the product 1 may be food associated with a farm. In one aspect, the product 1 may be fresh food. In one aspect, the product 1 may be frozen food. In one aspect, the product 1 may be unprocessed food. In one aspect, the product 1 may be processed food. In one aspect, the product 1 may be prepared food. In one aspect, the product 1 may be a food at any or plural stages consistent with the above.

In one aspect, the product 1 may be a manufactured product. In one aspect, the product 1 may be a product at any stage of manufacture. In one aspect, the product 1 may be a pharmaceutical product. In one aspect, the product 1 may be a medical device. In one aspect, the product 1 may be evidence for a criminal proceeding. In one aspect, the product 1 may be nonperishable consumables (napkins, dry goods, cups, supplies, and the like). In one aspect, the product 1 may be a temperature controlled or perishable consumable. In one aspect, the product 1 may be limited shelf life products.

Facility

In one aspect, the facility 200 may be a farm. For example, a farm may be defined as one or more arable farms, vegetable farms, fruit farms, dairy farm, pig farm, poultry farms, ranches, feedlots, orchards, and the like. In one aspect, the facility 200 may be a distribution channel such as a harvesting machine, tractor, bailer, combine harvester, truck, train, intermodal facility, and/or the like. In one aspect, the facility 200 may be a source of seafood. For example, a boat, a fisherman, and/or the like. In one aspect, the facility 200 may be a product preparation facility. For example, a product preparation facility may be a food preparation facility that may include a slaughterhouse, a canning facility, a kitchen, and/or the like.

In one aspect, the facility 200 may be a product distribution facility or distribution center. In one aspect, the facility 200 may be a retail facility. For example, a grocery store, a farmer's market, a quick service restaurant, a restaurant, a coffeehouse, a convenience store, and the like. In one aspect, the facility 200 may be a data aggregator, service provider, and/or the like. In one aspect, the facility 200 may be a services provider and/or the like. In one aspect, the facility 200 may be a transportation, logistics provider, and/or the like. In one aspect, the facility 200 may be an organization providing services such as Quality Assurance services, Regulatory services, Lab services, and the like services. In one aspect, the facility 200 may be any type of supply chain participant, which may or may not offer services, may or may not interact with products, may or may not interact with data on products, and/or the like service providers, transportation providers, and anyone else that may send data to the blockchain.

Product Related Information

The product related information 302 may include one or more of temperature information associated with the product 1, a unique identifier of the product 1, a location of the product 1, and the like.

In various aspects, the product related information 302 may include one or more of the following: the identification of the tracking device 300, date and time of collection of the product related information 302, an odor associated with an environment of the product 1, an identifier of the user of the tracking device 300, humidity information associated with the product 1, movement information associate with the product 1, received from information associated with the product 1, shipped to information associated with the product 1, product shelf life, product expiration date, product use by date, product best by date or equivalents thereof, characteristics to make certain certifications such as organic, grass fed, Non-GMO, standards and compliance related designations, and the like consistent with the disclosure.

In various aspects, the product related information 302 may further include one or more of the following: batch information associated with the product 1, lot information associated with the product 1, case information associated with the product 1, image information associated with the product 1, unit information associated with the product 1, time and transit information associated with the product 1, time and transit idling information associated with the product 1, and the like consistent with the disclosure. The product related information 302 may include algorithms to determine dynamic shelf life, remaining shelf life, and the like. Additionally, the product related information 302 may be utilized in conjunction with algorithms to determine dynamic shelf life, remaining shelf life, and the like. In this regard, aspects of the disclosure may include algorithms to determine replenishment points, safety stock information, similar supply chain demand/supply planning information, and the like. The product related information 302 may include processing business rules for consensus management and certification and the like. In this aspect, business rules may also include algorithms to determine acceptance criteria for product receipt and delivery. Additionally, the product related information 302 may include business rules triggering payment and invoicing confirmations and the like.

Temperature

In one aspect, the product related information 302 may include a current temperature of the product 1. In one aspect, the product related information 302 may include a current temperature of an environment of the product 1. In one aspect, the product related information 302 may include a historical temperature of an environment of the product 1. In one aspect, the product related information 302 may include a historical temperature of the product 1. In one aspect, the product related information 302 may include a historical high temperature of an environment of the product 1. In one aspect, the product related information 302 may include a historical high temperature of the product 1. In one aspect, the product related information 302 may include a historical low temperature of an environment of the product 1. In one aspect, the product related information 302 may include a historical low temperature of the product 1. In one aspect, the product related information 302 may include a historical temperature exception (exceeds a high temperature value and/or exceeds a low temperature value) of the product 1. In one aspect, the product related information 302 may include information obtained from an algorithm to determine temperature minutes (temperature out of limits multiplied by a dwell time at the out of temperature thresholds).

Movement/Location

In one aspect, the product related information 302 may include a location of the product 1. In one aspect, the product related information 302 may include a historical location of the product 1. In various aspects, the location may be the location of the facility 200, a location within the facility 200, the geographic location of the product 1, and/or the like.

In one aspect, the product related information 302 may include a historical movement of the product 1. In one aspect, the product related information 302 may include a historical movement exception (exceeds a high movement/acceleration threshold) of the product 1. In this regard, movement may include shock, dropping, and other possible damaging movement of the product 1.

Humidity

In one aspect, the product related information 302 may include a current humidity of an environment of the product 1. In one aspect, the product related information 302 may include a historical humidity of an environment of the product 1. In one aspect, the product related information 302 may include a historical high humidity of an environment of the product 1. In one aspect, the product related information 302 may include a historical low humidity of an environment of the product 1. In one aspect, the product related information 302 may include a historical humidity exception (exceeds a high humidity value and/or exceeds a low humidity value) of the product 1.

Figure 2:
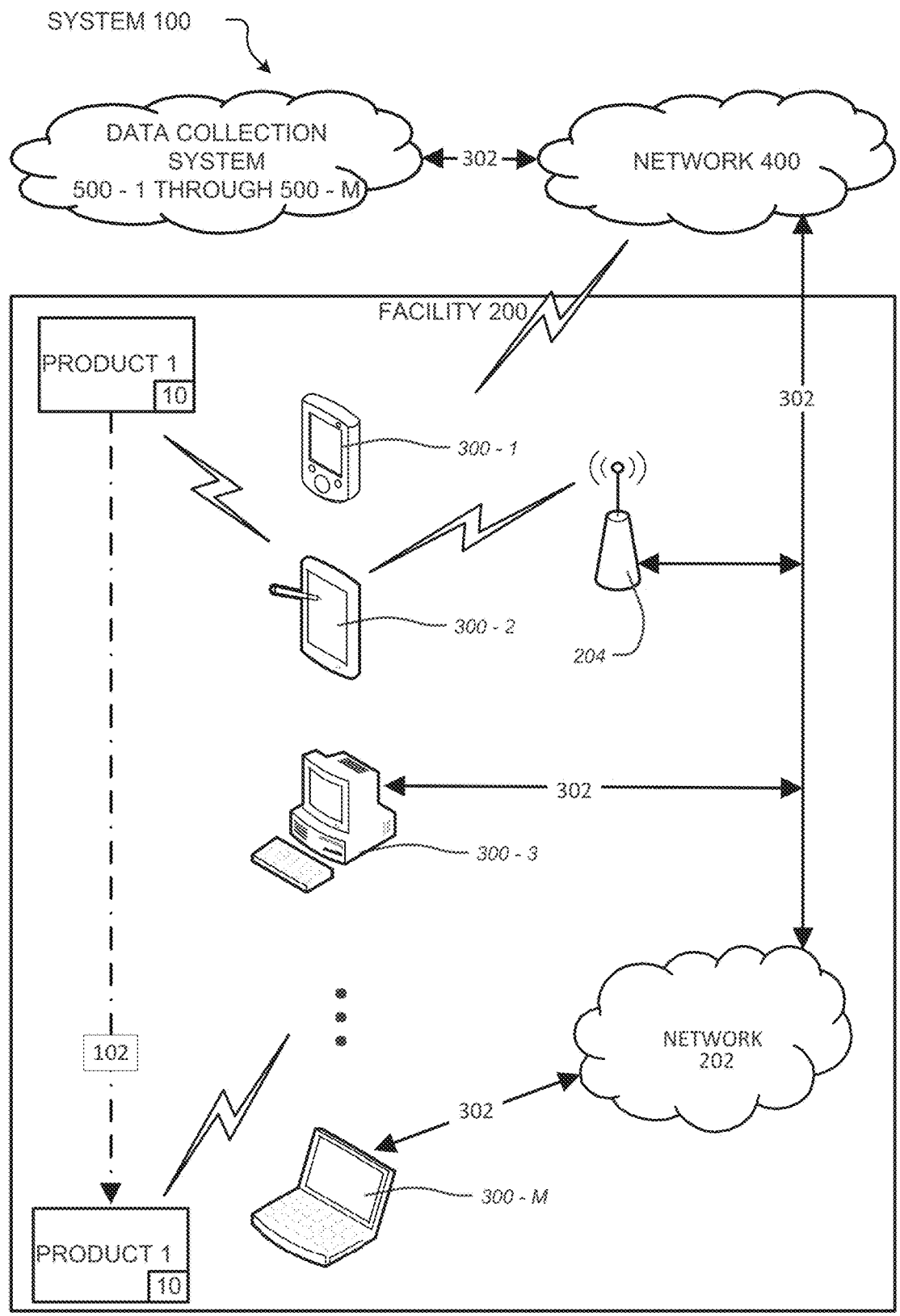
FIG. 2 illustrates the system with additional details of a facility and tracking devices according to the principles of the disclosure.

FIG. 2 illustrates the system with additional details of a facility according to the principles of the disclosure.

Figure 4:
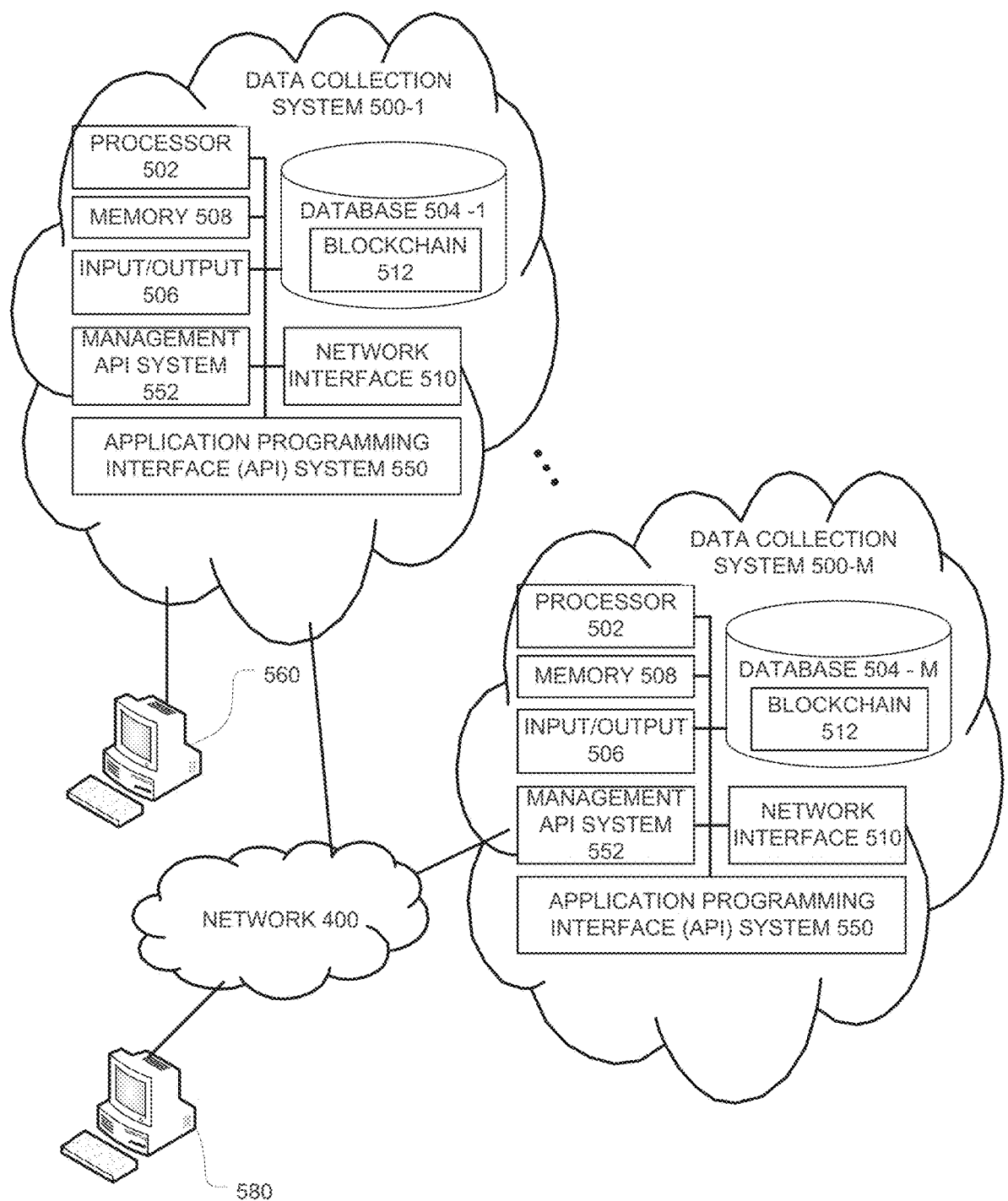
FIG. 4 illustrates the system with additional details of the data collection system according to the principles of the disclosure.

In particular, FIG. 2 illustrates further details of an exemplary one of the facility 200 and exemplary implementations of the tracking devices 300 implemented in the facility 200. As further described in detail below, the facility 200 may include a plurality of the tracking devices 300 each tracking the product 1 that may include the identifier 10 and obtaining the product related information 302 on the product 1. In particular, from time to time, the tracking device 300 may track the product 1 and obtain the product related information 302 on the product 1 and transmit the product related information 302 on the product 1 to the data collection system 500. In this regard, the data collection system 500 is configured and implemented to operate based on shared ledgers and simultaneous transmission of data to the various nodes or channel participants. Moreover, the data collection system 500 may be configured and implemented with multiple databases as illustrated in FIG. 4. In one aspect, the data collection system 500 may be configured and implemented for simultaneous replication of data utilizing data collection system 500-1 through data collection system 500-M by utilizing blockchain and a shared ledger or simultaneous replication of data for each permissioned viewer.

In this regard, in one aspect the tracking device 300 (300-2) may be implemented as a wireless device and may connect to a wireless access point 204. In other aspects, the tracking device 300 may be implemented as a wireless device (300-1) and may connect directly to a wireless network associated with the network 400. In other aspects, the tracking device 300 may be implemented as a wired implementation (300-M) of the tracking device 300 and may connect directly to a network that connects to the network 400. In other aspects, the tracking device 300 may be implemented as a wired tracking device (300-3) and may connect directly to the network 400. Each of the wired/wireless connections may utilize a transceiver and protocols associated with a communication channel as defined herein. In some aspects, the tracking device 300 may connect to an IDF (intermediate distribution frame). In some aspects, the IDF may be implemented by the network 202. In some aspects, the IDF may be implemented by the tracking device 300. The IDF may be implemented as a free-standing or wall-mounted rack for managing and interconnecting the telecommunications between the tracking devices 300, the network 202, the network 400, a main distribution frame (MDF), the data collection system 500, and the like. In this regard, the IDF and MDF may be configured and implemented to utilize the disclosed blockchain concepts of simultaneously replicating data onto multiple shared ledgers. Additionally, the data collection system 500 may be configured with multiple replications of the database and/or multiple replications of multiple databases utilizing blockchain and integration layers.

Figure 3:
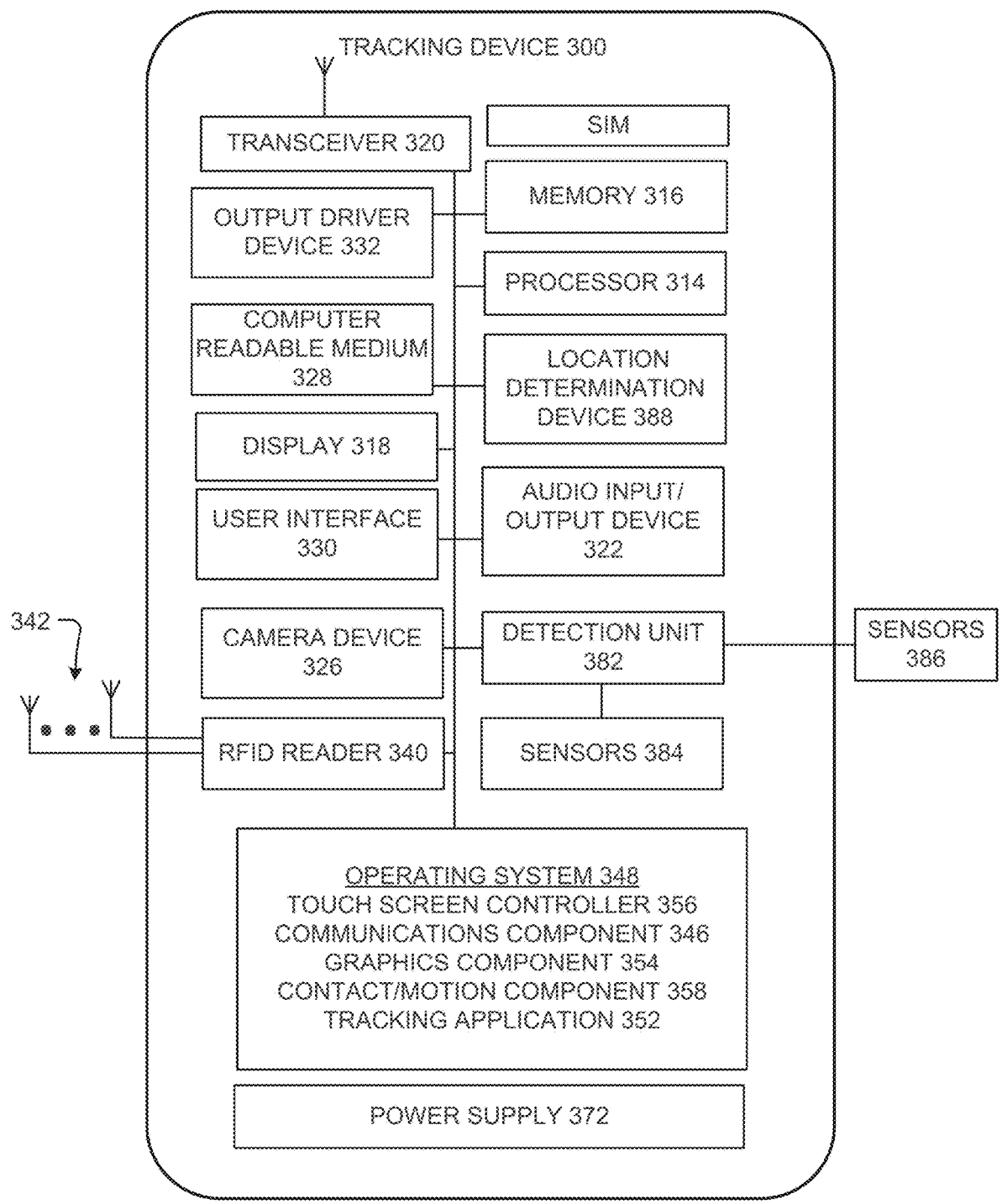
FIG. 3 illustrates exemplary details of a tracking device utilized in the system according to the principles of the disclosure.

FIG. 3 illustrates exemplary details of a tracking device utilized in the system according to the principles of the disclosure.

The tracking device 300 may have a number of different implementations. In one aspect, the tracking device 300 may be a fixed or static installation within the facility 200. For example, the tracking device 300 may be placed at numerous locations within the facility 200 to detect the identifier 10 of the product 1 along with the product related information 302. In one aspect, the tracking device 300 may be a handheld device utilized by employees within the facility 200. For example, the tracking device 300 may be carried by one or more employees within the facility 200 to detect the identifier 10 of the product 1 along with the product related information 302. In one aspect, the tracking device 300 may be a fixed or static installation of an Internet of things (IoT) implemented device within the facility 200. For example, the tracking device 300 may be placed at numerous locations within the facility 200 to detect the identifier 10 of the product 1 along with the product related information 302. In one aspect, the tracking device 300 may be an Internet of things (IoT) implemented device within the facility 200 implemented as a transportation component such as a delivery truck. In this regard, the disclosure contemplates various remote devices such as an Internet of things (IoT) implemented devices in transportation trucks, remote sensors such as an Internet of things (IoT) implemented devices placed on the trucks, remote sensors and/or an Internet of things (IoT) implemented devices placed at a physical location, and the like.

The various implementations of the tracking device 300 may include one or more of the features described below. However, the tracking device 300 need not include all of the features. The number of features implemented by the tracking device 300 may depend on its desired functionality, location, implementation, and the like.

The tracking device 300 may include a processor 314, a memory 316, and the like. The processor 314 may be a central processing unit, chipset, microprocessor, dedicated hardware, and/or the like configured to execute instructions including instructions related to software programs.

The tracking device 300 may further include in the memory 316 or separate from the memory 316, a computer readable memory 328, an operating system 348, a communication component 346, a contact/motion component 358, a touchscreen controller 356, a graphics component 354, and the like. The operating system 348 together with the various components providing software functionality for each of the components of the tracking device 300. The tracking device 300 may further include a read-only memory (ROM) and a power supply 372 such as a battery or a wired connection to a power source. In some aspects, the power supply 372 may be a battery such as nickel cadmium, nickel metal hydride, lead acid, lithium ion, lithium ion polymer, and the like.

The memory 316 may include a high-speed random-access memory. Also, the memory 316 may be a non-volatile memory, such as magnetic fixed disk storage, flash memory and/or the like. The various components of the tracking device 300 may be connected through various communication lines including a data bus.

The product 1 may include the identifier 10. The identifier 10 may be implemented as one or more of a radiofrequency identification (RFID) device, a barcode, a QR code, a Data Matrix (DM) code, and/or the like. In one aspect, the identifier 10 may be an alphanumeric code that may be manually input to the tracking device 300. In one aspect, the identifier 10 may be a machine-readable code that may be configured to be readable by the tracking device 300.

In one aspect, the tracking device 300 may include a RFID reader 340 configured to generate interrogating radio waves. The interrogating radio waves from the RFID reader 340 may be received by the identifier 10 implemented as an RFID device. In this aspect, the RFID device may automatically identify the identifier 10 attached to product 1 in response to the interrogating radio waves from the RFID reader 340. The identifier 10 may contain and transmit electronically-stored information that includes the product related information 302. In one aspect, the identifier 10 may collect energy from the RFID reader 340 transmitting interrogating radio waves. In one aspect, the RFID device may have a local power source (such as a battery) and may operate hundreds of meters from the RFID reader 340.

The identifier 10 may include or connect to a number of sensors to detect a physical characteristic. The identifier 10 may implement one or more of an accelerometer, gyroscope, altitude sensor, temperature sensor, proximity sensor, odor sensor, IR sensor (infrared sensor), pressure sensor, light sensor, ultrasonic sensor, smoke sensor, gas sensor, alcohol sensor, touch sensor, color sensor, humidity sensor, tilt sensor, flow sensor, level sensor, motion sensor, and/or the like. The identifier 10 may further include analog-to-digital converters, filters, and the like to process the signals associated with any of the sensors. In response to the RFID reader 340, the identifier 10 may provide one or more of the above noted physical quantity sensed by the sensors as the product related information 302 to the tracking device 300. In one aspect, the temperature sensor may be a thermocouple, a thermistor, and/or the like. In one aspect, the product related information 302 may include an odor of the environment of the product 1. In this aspect, there may be an odor associated with a location within the facility 200. In this aspect, there may be an odor associated with a ventilation system within the facility 200. In one aspect, an odor sensor may be implemented as an electronic nose and may include a sample delivery system, a detection system, a computing system. In one aspect, the odor sensor may be implemented as an electronic nose that may be implemented as one or more of a metal-oxide-semiconductor (MOSFET) device, a device having conducting polymers-organic polymers that conduct electricity, a polymer composite device, a quartz crystal microbalance device, a surface acoustic wave (SAW) device, and/or the like configured for detecting a pathogen, a disease, and/or the like.

In some aspects, the RFID reader 340 and the identifier 10 implemented as an RFID device may include one or more antennas 342 separate from the tracking device 300. In some aspects, the RFID reader 340 may have multiport capability to connect to multiple antennas 342 configured for operation to implement RFID technology. In some aspects, the RFID reader 340 may be mounted within a NEMA (National Electrical Manufacturers Association) enclosure that may provide various grades of electrical enclosures typically used in industrial applications to protect against personal access to hazardous parts, and additional type-dependent designated environmental conditions. In some aspects, the RFID reader 340 may be implemented as a RFID gate. In some aspects, the RFID reader 340 may be implemented as a directional gate.

In some aspects, the identifier 10 implemented as an RFID device may be produced at one of the facilities 200. In one aspect, the identifier 10 implemented as an RFID may be assigned and physically attached to the product 1. In one aspect, an RFID printer may print the identifier 10 implemented as an RFID and the identifier 10 may be assigned and physically attached to the product 1. As the product 1 is processed at the facilities 200, a new identifier 10 may be printed and physically attached to the product 1 and the product related information 302 may be updated to associate a previous one of the identifier 10 to the new one of the identifier 10.

The tracking device 300 may include a camera device 326. The camera device 326 can include one or more cameras to provide visual input. The camera device 326 can also capture video in combination with audio from a microphone of the audio input/output device 322. The camera device 326 may include a charge coupled device (CCD), CMOS image sensors, Back Side Illuminated CMOS, and/or the like. Images captured by the camera device 326 may be converted and stored in various formats including a JPEG file format, RAW feature format such as the Android (operating system) 5.0 Lollipop, and the like. In this regard, as noted above, the product related information 302 may include images of the product 1 as well as images of an environment of the product 1. In this regard, the tracking device 300 may automatically capture an image of the product 1 as the product related information 302. In other aspects, the tracking device 300 may be operated to capture an image of the product 1 if a user determines there are issues related to the product 1. For example, the issues may include damage, leakage, mold, box open, other defects, and the like.

In one aspect, the identifier 10 may be implemented as a QR code. In a particular aspect, the camera device 326 may include functionality as a barcode reader or a QR code reader. A QR code (Quick Response Code) is a type of matrix barcode (or two-dimensional barcode). The barcode is a machine-readable optical label that contains information about the product 1 to which it is attached. A QR code uses a number of standardized encoding modes including numeric, alphanumeric, byte/binary, and the like to efficiently store the product related information 302. The QR code may include black modules arranged in a square grid on a white background, which can be read by the camera device 326 or other imaging device and processed using Reed-Solomon error correction until the image can be appropriately interpreted. The product related information 302 may then be extracted from patterns that are present in both horizontal and vertical components of the image.

In one aspect, the identifier 10 may be implemented as a barcode. In a particular aspect, the camera device 326 may include functionality as a Universal Product Code (UPC) reader. The UPC is a barcode symbology utilizing protocols such as UPC-A, UPC-E, EAN, UPC-B, UPC-C UPC-D, UPC-2, UPC-5, and the like.

In one aspect, the identifier 10 may be implemented as a Data Matrix (DM) code. In a particular aspect, the camera device 326 may include functionality as a Data Matrix code reader. A Data Matrix code is a two-dimensional matrix barcode including black and white "cells" or modules arranged in either a square or rectangular pattern. The Data Matrix code may be implemented with the ECC 200 version of Data Matrix and include Reed-Solomon codes for error and erasure recovery. Other protocols and/or versions of Data Matrix are contemplated as well.

Additionally, the tracking device 300 may include an audio input/output device 322. The audio input/output device 322 may include speakers, speaker outputs, and the like, providing sound output; and may include microphones, microphone inputs, and the like, for receiving sound inputs. The audio input/output device 322 may include an analog to digital converter and a digital to audio converter for audio input and output functions respectively. In one aspect, the audio input/output device 322 may generate and output audio instructions generated by the tracking device 300. In one aspect, the audio input/output device 322 may receive and respond to audio instructions utilizing voice recognition processed by the tracking device 300.

The tracking device 300 may include a transceiver 320 and the like. The transceiver 320 of the tracking device 300 may provide radio and signal processing as needed to access a network 202, the network 400, and/or the like for services over a communication channel as defined herein. In one aspect, the network 202 may be implemented as the intermediate distribution frame (IDF). The processor 314 and the transceiver 320 may be configured to process instruction functions, data transfer, provide other services, transmit the product related information 302 to the data collection system 500, and the like.

In some aspects, the tracking device 300 may include a display 318, a user interface 330, and the like. The display 318 may be a liquid crystal display having a backlight to illuminate the various color liquid crystals to provide a colorful display. In some aspects, the display 318 may be a light-emitting diode display (LED), an electroluminescent display (ELD), a plasma display panel (PDP), a liquid crystal display (LCD), an organic light-emitting diode display (OLED), an active-matrix organic light-emitting diode (AMOLED) display, an IPS (In-plane switching) liquid crystal display (LCD), or any other display technology. The user interface 330 may be any type of physical input having one or more buttons, switches, and the like and/or may be implemented as a touchscreen.

The touchscreen of the disclosure may be implemented in the display 318 and may detect a presence and location of a touch of a user within the display area. For example, touching the display 318 of the tracking device 300 with a finger or hand. The touchscreen may also sense other passive objects, such as a stylus. In one aspect, a user can enter the product related information 302 into the display 318 of the tracking device 300 utilizing the touchscreen. In one aspect, if the identifier 10 is damaged or otherwise inoperative, a user can enter the product related information 302 into the display 318 of the tracking device 300 utilizing the touchscreen.

In operation, the display 318 may display various objects associated with applications for execution by the processor 314. In this regard, a user may touch the display 318, and in particular the touchscreen, to interact with the objects. For example, touching an object may execute an application in the processor 314 associated with the object that is stored in memory 316. Additionally or alternatively, touching an object may open a menu of options to be selected by the user. The display 318 may include a plurality of the objects for the user to interact with. Moreover, the display 318 may include a plurality of screens. The display 318 showing one screen at a time. The user may interact with the display 318 to move a screen into view on the display 318. Various objects may be located in the each of the screens.

The touchscreen may be implemented as a resistive touchscreen, a surface acoustic wave touch screen, a capacitive touch screen, a surface capacitance touchscreen, a projected capacitive touch screen, self-capacitance sensors, infrared sensors, dispersive signal technology, acoustic pulse recognition, and/or the like.

The tracking device 300 may include a detection unit 382. The detection unit 382 may include or connect to a number of internal sensors 384 and/or external sensors 386 to detect a physical quantity that may be associated with the product related information 302. The detection unit 382 may be implemented to receive the sensor input from any one or more of an accelerometer, gyroscope, altitude sensor, temperature sensor, proximity sensor, odor sensor, IR sensor (infrared sensor), pressure sensor, light sensor, ultrasonic sensor, smoke sensor, gas sensor, alcohol sensor, touch sensor, color sensor, humidity sensor, tilt sensor, flow sensor, level sensor, motion sensor, and/or the like. The detection unit 382 may further include analog-to-digital converters, filters, and the like to process the signals associated with any of the above noted sensors. In one aspect, the detection unit 382 may obtain one or more of the physical characteristics noted above and include the same as product related information 302.

The tracking device 300 may include an output driver device 332. The output driver device 332 may be configured to provide a drive signal to control, initiate, and the like a component associated with the tracking device 300. In one aspect, the tracking device 300 may utilize the output driver device 332 to provide operation to the component within the facility 200.

The computer readable memory 328 may be configured to store a tracking application 352. For the purposes of this disclosure, the computer readable memory 328 stores computer data, which may include computer program code that may be executable by the processor 314 of the tracking device 300 in machine readable form. By way of example, and not limitation, the computer readable memory 328 may include computer readable storage media, for example tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules, or other data. In one or more aspects, the actions and/or events of a method, algorithm, or module may reside as one or any combination or set of codes and/or instructions on a computer readable memory 328 or machine readable medium, which may be incorporated into a computer program product. In one aspect, the tracking application 352 may be implemented as a non-transitory computer program product stored on a recording medium.

According to another aspect of the disclosure, the tracking device 300 may include a location determination device 388 to estimate the location of the tracking device 300 based, at least in part, on a global navigation satellite system (GNSS). In another aspect, a wireless network may implement location determination based on a specific cell in which the tracking device 300 connects and provide this information to the system 100. In yet another aspect, the wireless network may obtain location determination based on triangulation with respect to a plurality of cells in which the tracking device 300 receives signals and provide this information to the system 100. In yet another aspect, the wireless network implementing wireless fidelity may obtain location determination in which the tracking device 300 receives signals and provide this information to the system 100. In yet another aspect, the tracking device 300 may be assigned to a particular facility 200 having a known location that is set in the tracking device 300.

In one aspect, the tracking device 300 may be implemented as an Internet of things (IoT) device embedded with electronics, software, sensors, actuators, network connectivity, and/or the like, which enable the tracking device 300 to connect and exchange data. The IoT implementation of the tracking device 300 may allow objects to be sensed or controlled remotely across a network infrastructure, which provides direct integration of the physical world as it relates to the facility 200 and the product 1 into computer-based systems, such as the data collection system 500 resulting in improved efficiency, accuracy, and economic benefit in addition to reduced human intervention.

In one aspect, the tracking device 300 may be implemented in an industrial implementation, a connected health related implementation, a smart retail implementation, a smart supply chain implementation, a smart farming implementation, a smart restaurant implementation, a smart medical facility implementation, a smart pharmacy implementation, and the like. The tracking device 300 may be configured to sense, control, be controlled, and the like remotely across a wired/wireless network infrastructure, creating opportunities for more direct integration of the physical world into computer-based systems, and resulting in improved efficiency, accuracy and economic benefit in addition to reduced human intervention.

The tracking device 300 may connect to the network 400, the network 202, a wireless network associated with the wireless access point 204, a wireless network implemented by the network 400, and/or the like that may encompass any type of wired or wireless network services for the use of the tracking device 300, such as the Global System for Mobile Communication (GSM) network, Code-Division Multiple Access (CDMA) network, GSM/EDGE and UMTS/HSPA network technologies, Long Term Evolution (LTE), 5G (5th generation mobile networks or 5th generation wireless systems), WiMAX, HSPA+, W-CDMA (Wideband Code-Division Multiple Access), CDMA2000 (also known as C2K or IMT Multi-Carrier (IMT-MC)), Wireless Fidelity (Wi-Fi), Bluetooth, a communication channel as defined herein, and/or the like, and/or a combination of two or more thereof, that may utilize the teachings of the disclosure to allow the tracking device 300 to connect to a wired and/or wireless network to exchange data to the system 100, with the data collection system 500, and/or the like.

In this regard, the product related information 302, data, information, instructions, and the like may be exchanged between the network 202, the network 400, the tracking device 300, the data collection system 500, and the like over a communication channel as defined herein.

The tracking device 300 of the disclosure as described provides increased efficiency, connectivity, control, proficiency, information, and the like with respect to the product related information 302 of the product 1.

FIG. 4 illustrates the system with additional details of the data collection system according to the principles of the disclosure.

In particular, FIG. 4 illustrates an exemplary implementation of the data collection system 500. The data collection system 500 may be implemented by one or more servers, processors 502, databases 504, network interfaces 510, input output devices 506, memory 508, and the like.

In one aspect, the data collection system 500 may be configured as centralized computer. In one aspect, the data collection system 500 may be configured as a server. In one aspect, the data collection system 500 may be configured as a decentralized server. In one aspect, the data collection system 500 may be configured as a decentralized computer.

In one aspect, the data collection system 500 may be configured to communicate over the network 400 utilizing encryption; and the data collection system 500 may be configured for decryption of data received over the network 400. The processor 502 and/or the network interface 510 may provide the encryption and decryption functionality. Additionally, the tracking device 300 may likewise be configured for and provide the encryption and decryption functionality as described herein. In one aspect, the encryption may include a process of encoding a message, information, the product related information 302, and/or the like in such a way that only authorized parties can access it and those who are not authorized cannot. In one aspect, the encryption may include an encryption scheme, the intended information or message, referred to as plaintext, is encrypted using an encryption algorithm, which may be a cipher, generating ciphertext that can be read only if decrypted. In one aspect, the encryption scheme may use a pseudo-random encryption key generated by an algorithm. In symmetric-key schemes, the encryption and decryption keys may be the same. Communicating parties must have the same key in order to achieve secure communication. In one aspect, the encryption scheme may be a public-key encryption scheme where the encryption key is published for anyone to use and encrypt messages. However, only the receiving party has access to the decryption key that enables messages to be read.

In one aspect, the data collection system 500 may be configured as cloud-based system. In one aspect, the data collection system 500 may be configured as non-cloud-based system. In one aspect, the data collection system 500 may be configured as a transformation services layer, micro services, and/or the like and equivalents thereof.

In one aspect, the data collection system 500 may be configured to store in the database 504 all the above noted product related information 302 from the tracking devices 300. In this regard, the data collection system 500 may be configured to connect directly to a computer 560 or connect over the network 400 to computer 580 in order to provide the stored product related information 302 from the database 504.

In particular aspects, the data collection system 500 in response to a query from the computer 560 and/or the computer 580 may be configured to allow searching for any of the above noted captured information that includes the product related information 302 obtained from the tracking devices 300 in any one or more of the facilities 200. In this regard, the query to the data collection system 500 may include a query for a particular product 1 and the data collection system 500 in conjunction with the database 504 may obtain and transmit the response to the computer 560 and/or the computer 580. In particular, the query can be based on the particular product 1, the particular facility 200 (farm, distribution center, restaurant, and/or the like), by case number, by lot number, by batch number, by item number, product expiration dates, product use by dates, and/or the like.

In particular aspects, the data collection system 500 in response to a query from the computer 560 and/or the computer 580 may be configured to provide inventory determination, replacement determination, supply chain determination, consumption metrics, inventory counts, gross inventory, forecasted inventory, and the like (inventory related information) based on the above noted captured information that includes the product related information 302 obtained from the tracking device 300 in any one or more of the facilities 200. In this regard, the query to the data collection system 500 may include a query for the inventory related information and the data collection system 500 in conjunction with the database 504 may obtain and transmit the response to the computer 560 and/or the computer 580. In other aspects, the data collection system 500 may monitor an inventory at each facility 200. Moreover, the data collection system 500 may determine and forecast future inventory needs based on historical consumption of the inventory. Additionally, the data collection system 500 may determine inventory replacement for one or more of the facilities 200. Finally, the data collection system may communicate requests to provide inventory for one or more the facilities 200. In some aspects, the data collection system 500 may be configured with artificial intelligence in order to assist in the inventory analysis. The artificial intelligence may utilize any number of approaches including one or more of cybernetics and brain simulation, symbolic, cognitive simulation, logic-based, anti-logic, knowledge-based, sub-symbolic, embodied intelligence, computational intelligence and soft computing, machine learning and statistics, and the like in order to assist in the inventory analysis.

In particular aspects, the data collection system 500 in response to a query from the computer 560 and/or the computer 580 may be configured to provide traceability functions based on the above noted captured information that includes the product related information 302 obtained from the tracking devices 300 in any one or more of the facilities 200. In this regard, the query to the data collection system 500 may include a query for tracing a particular one or more of the product 1 and the data collection system 500 in conjunction with the database 504 may obtain and transmit the response to the computer 560 and/or the computer 580. In particular, the traceability functionality query can be based on the particular product 1, the particular facility 200 (farm, distribution center, restaurant, and/or the like), by case number, by lot number, by batch number, by item number, and/or the like.

In particular aspects, the data collection system 500 in response to a query from the computer 560 and/or the computer 580 may be configured to provide for tracking functions based on the above noted captured information that includes the product related information 302 obtained from the tracking devices 300 in any one or more of the facilities 200. In this regard, the query to the data collection system 500 may include a query for tracking a particular product 1 and the data collection system 500 in conjunction with the database 504 may obtain and transmit the response to the computer 560 and/or the computer 580. In particular, the tracking functionality query can be based on the particular product 1, the particular facility 200 (farm, distribution center, restaurant, and/or the like), by case number, by lot number, by batch number, by item number, and/or the like.

In particular aspects, the data collection system 500 in response to a query from the computer 560 and/or the computer 580 may be configured for pathogen/disease determination from captured images obtained from the tracking device 300. In this regard, the captured images obtained from the tracking device 300 together with the product related information 302 may be analyzed by the data collection system 500 for a determination of indications of a pathogen, a disease, and/or the like. In some aspects, the captured images may be captured in conjunction with the system utilizing ultraviolet light, infrared light, and/or the like. In this aspect, the camera device 326 may be configured for capturing images based on ultraviolet light, infrared light, and/or the like.

In some aspects, the data collection system 500 may be configured with artificial intelligence in order to assist in the determination of a pathogen, disease, and/or the like. The artificial intelligence may utilize any number of approaches including one or more of cybernetics and brain simulation, symbolic, cognitive simulation, logic-based, anti-logic, knowledge-based, sub-symbolic, embodied intelligence, computational intelligence and soft computing, machine learning and statistics, and the like in order to assist in the determination of a pathogen, disease, and/or the like.

In some aspects, the determination of a pathogen, disease, and/or the like may be determined by the data collection system 500 by comparison of the captured images to pathogen or disease image information stored in the database 504. In this regard, the pathogen or disease image information may include signature spectral images, signature colors in images, signature shapes in images, and the like consistent with a pathogen or disease and the comparison to the captured images may show an indication of a disease or pathogen.

In particular aspects, the data collection system 500 and/or the database 504 may utilize and implement blockchain 512 technology. In this regard, the data collection system 500 and/or the database 504 may take the received product related information 302 as a list of records, that may be defined as blocks. In particular, each of the blocks of the product related information 302 may be linked using cryptography. Each block may contain a cryptographic hash of the previous block, a timestamp, and the product related information 302. The blockchain 512 may be managed by the data collection system 500 adhering to a protocol for inter-node communication and validation of new blocks. In some aspects, the resulting blockchain 512 of the product related information 302 may form a blockchain ledger that may not be easily modified, changed, and the like to ensure a higher level of security and data confidence. In one aspect, the block chain 512 may be implemented as a public blockchain, a private blockchain, a consortium blockchain, and/or the like.

In one aspect, the data collection system 500 may include a functional application programming interface (API) system 550. In one aspect, the data collection system 500 may include a management application programming interface (API) system 552. In one aspect, the data collection system 500 may include the management API system 552 and the functional application programming interface (API) system 550.

In some aspects, the APIs of the functional API system 550 and the management API system 552 may include a set of subroutine definitions, protocols, tools, and the like. These may include a set of clearly defined methods of communication between various software components including the tracking devices 300 and the data collection system 500. The APIs may be for a web-based system, an operating system, a database system, computer hardware, a software library, and/or the like. In some aspects, the APIs may include a specification that can take many forms, but may include specifications for routines, data structures, object classes, variables, remote calls, and/or the like. The APIs may be implemented by POSIX, Windows API, ASPI, and the like.

The functional API system 550 may implement or connect to an on-demand cloud computing platform. The functional API system 550 may allow subscribers to have at their disposal a full-fledged virtual cluster of computers, available all the time, through the internet. The functional API system 550 may implement virtual computers that may include a number of the attributes of a real computer including a central processing unit (CPU), graphics processing unit (GPU), Random-access memory (RAM), hard-disk storage, solid-state drive (SSD) storage, and/or the like. The functional API system 550 may include a choice of operating systems and networking. The functional API system 550 may have pre-loaded application software such as web servers, databases, and the like. The functional API system 550 may also virtualize its console I/O (keyboard, display, and mouse), allowing users to connect to the data collection system 500 using a browser, and/or the like. The browser may act as a window into the virtual computer, letting subscribers log-in, configure, and the like.

In some aspects of the disclosure, one or more of the management API system 552 and/or the data collection system 500 may include an information portal, query portal, and/or the like that may be implemented as a web portal. The information portal may be a specially designed portal that brings information from diverse sources including the tracking devices 300 and/or the data collection system 500. In some aspects, each information source may receive a dedicated area on a page for displaying information (a portlet). In some aspects, the portal may include mashups and intranet "dashboards." The portal may use the application programming interface (API). The portal may provide a way for enterprises and organizations with access control, modification, procedures, and the like for multiple applications and databases as it relates to the product 1, the facilities 200, the tracking devices 300, the data collection system 500, and/or the like. The features available may be restricted to an authorized and authenticated user (employee, member).

In one or more aspects, the management API system 552 and/or the functional API system 550 may be configured to run commands for the tracking device 300, the data collection system 500, and/or the like on Windows, macOS, Linux, and/or the like. These commands may allow the creation and management of the tracking device 300, the data collection system 500, certificates, rules, and policies. In one or more aspects, the management API system 552 and/or the functional API system 550 may be configured to build IoT applications for the tracking devices 300 using HTTP or HTTPS requests. These API actions allow the program creation and management of the tracking devices 300, certificates, rules, and policies. In one or more aspects, the management API system 552 and/or the functional API system 550 may be configured to build IoT applications using language-specific APIs. The associated SDKs may wrap the HTTP/HTTPS API and allow programming in any of the supported languages. In one or more aspects, the management API system 552 and/or the functional API system 550 may be configured to build applications that run on the tracking device 300, the data collection system 500, and the like that send messages to and receive messages from the management API system 552, the functional API system 550, and/or the tracking device 300.

In one aspect, the data collection system 500 may include a transformation service. The transformation service may be a system interface used to communicate between IoT devices and the blockchain. The transformation service may incorporate business logic, perform blockchain queries, and identify key RFID data attributes necessary for creating blockchain transactions. Using these functionalities, the transformation service may be responsible for parsing RFID messages and transforming them into XMLs that may include GS1 formatted data.

The transformation process may begin as RFID messages having one or more of a zone, read time, and observed Electronic Product Codes (EPCs) that may be published to the service. This information provides the transformation service enough information to infer the event type and identify the data attributes required for the blockchain message. The transformation service may then query the blockchain to determine data inputs for elements not provided in the RFID read, such as source location.

In addition to publishing the event messages to blockchain, the transformation service may also be depended upon to create temperature payloads. Any time an event is transmitted to the blockchain, the transformation services query the blockchain for the previous timestamp of a previous event. Using the timestamps from a current and the previous event, the service may query the IoT device(s) at the event's location and they create a temperature payload that is sent to the blockchain. This temperature information may be the basis for temperature monitoring and the input that triggers a smart contract to run. In this regard, the system may contain, implement, and utilize smart contracts to manage product temperature rules and inventory discrepancies.

In some aspects, the data collection system 500 may be responsive to phone calls (voice calls) from authorized users. In this regard, the data collection system 500 may utilize an interactive voice response system to provide product related data for the product 1, ordering of the product 1 for a particular facility 200, inventory information, tracking queries, traceability queries, and the like when computer access is limited. In some aspects, this may be utilized for inventory ordering, and the like.

Figure 5:
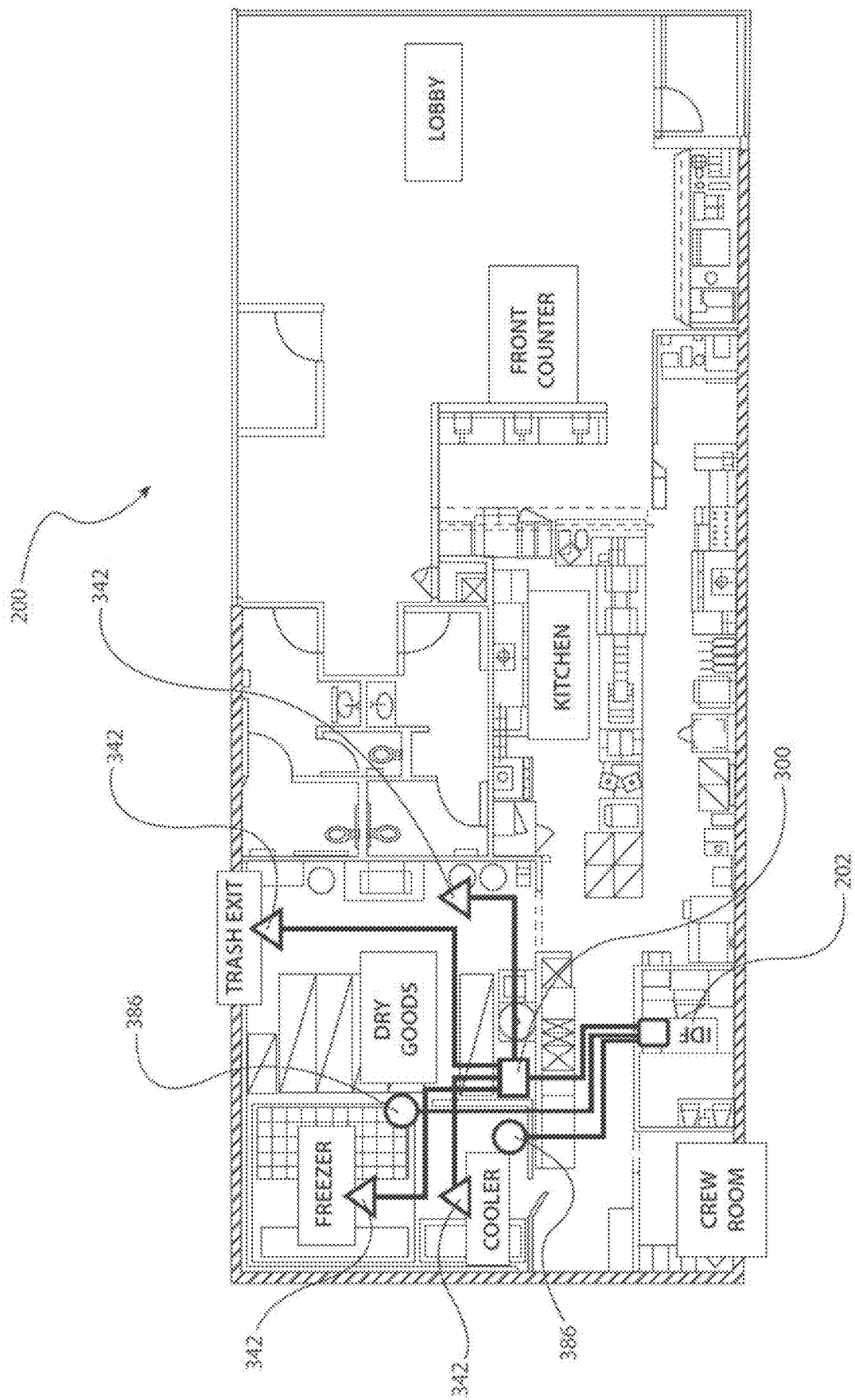
FIG. 5 illustrates the system in a particular implementation of a facility with tracking devices according to the principles of the disclosure.

FIG. 5 illustrates the system in a particular implementation of a facility with tracking devices according to the principles of the disclosure.

In particular, FIG. 5 illustrates a facility 200 that may be a restaurant. As further illustrated in FIG. 5, the facility 200 (restaurant) may include a lobby, a front counter, a kitchen, a crew room, a cooler, a freezer, a trash exit, a dry goods storage area, a receiving entrance, and the like. The tracking device 300 may be located within the facility 200. Although only one tracking device 300 is illustrated in FIG. 5, other aspects may include a plurality of the tracking devices 300.

In one aspect, the tracking device 300 may include an antenna 342 in the freezer together with an external sensor 386. In one aspect, the external sensor 386 in the freezer may be a temperature sensor. However, consistent with the disclosure, the external sensor 386 may sense other physical characteristics as well.

In one aspect, the tracking device 300 may include an antenna 342 in the cooler together with an external sensor 386. In one aspect, the external sensor 386 in the cooler may be a temperature sensor. However, consistent with the disclosure, the external sensor 386 may sense other physical characteristics as well.

In one aspect, the tracking device 300 may include an antenna 342 in the dry goods storage area; and an antenna 342 at the trash exit. Additionally, the facility 200 may include an antenna 342 connected to the tracking device 300 in other areas of the facility 200 including the kitchen, the crew room, the receiving entrance, and other areas of the facility 200.

In the implementation illustrated in FIG. 5, the product 1 that is stored in the freezer may be identified by its associated identifier 10 by the antenna 342 in the freezer. While the product 1 is in the freezer, the product related information 302 including information from the external sensor 386 may be obtained by the tracking device 300 and sent to the data collection system 500. As the product 1 exits the freezer, the antenna 342 may detect the movement and update the product related information 302 and send the same to the data collection system 500.

Likewise, the product 1 that is stored in the cooler, the dry goods storage area, the kitchen, the crew room, and other areas of the facility 200 may be identified by its associated identifier 10 by the antenna 342 in these areas. While the product 1 is in the various areas, the product related information 302 including information from the external sensor 386 may be obtained by the tracking device 300 and sent to the data collection system 500. As the product 1 exits these areas, the antenna 342 may detect the movement and update the product related information 302 and send the same to the data collection system 500. In one aspect, the detection of movement may be in response to a motion sensor. In one aspect, the detection of movement may be in response to the RFID reader 340 sensing movement of the product 1 and its associated identifier 10.

Likewise, when product 1 arrives at the facility 200 the product 1 may be identified by its associated identifier 10 by the antenna 342 at arrival. While the product 1 arrives, the product related information 302 including information from the external sensor 386 may be obtained by the tracking device 300 and sent to the data collection system 500.

In a further aspect, as the product 1 is consumed the remaining packaging that still includes the identifier 10 may be taken by an employee of the facility 200 to a trash corral via the trash exit. The antenna 342 may detect this action as the packaging with the identifier 10 leaves the facility 200 via the trash exit. As the identifier 10 exits the facility 200, the antenna 342 may detect the movement and update the product related information 302 and send the same to the data collection system 500. In one aspect, the detection of movement may be in response to a motion sensor. In one aspect, the detection of movement may be in response to the RFID reader 340 sensing movement of the product 1 and its associated identifier 10.

In some aspects, the identifier 10 may further include embedded sensors as described above. In this aspect, the product related information 302 may include information from the embedded sensors that may be sent to the data collection system 500.

In some aspects, the tracking device 300 may be handheld. In this aspect, the product 1 may be identified by its associated identifier 10 by the antenna 342 of the handheld implementation of the tracking device 300. Further in this aspect, the product related information 302 including information from the internal sensor 384 may be obtained by the tracking device 300 and sent to the data collection system 500. For example, the employee holding the handheld implementation of the tracking device 300 may enter the freezer and identify the product 1 by its associated identifier 10 and capture sensor readings, such as the temperature of the freezer, with the tracking device 300.

In some aspects, the tracking device 300 may implement the camera device 326. In these aspects, the product 1 may be identified by its associated identifier 10 by the antenna 342 of the tracking device 300. Alternatively, the product 1 may be identified by its associated identifier 10 by the camera device 326 of the tracking device 300. Further in this aspect, the product related information 302 including information from the camera device 326 may be obtained by the tracking device 300 and sent to the data collection system 500. For example, the tracking device 300 may be operated to capture an image of the product 1 if there are visually issues related to the product 1. For example, the issues may include damage, leakage, mold, and the like. In another aspect, the tracking device 300 may be implemented in the kitchen and the camera device 326 may capture images of preparation surfaces and the like in the kitchen. The product related information 302 that includes images captured by the camera device 326 may be sent to the data collection system 500. In a particular aspect, the data collection system 500 may analyze the images from the camera device 326 to determine if the food preparation surfaces in the kitchen include a pathogen, a disease, and/or the like as described herein. Similarly, the data collection system 500 may analyze the images of the product 1 from the camera device 326 to determine if the product 1 includes a pathogen, disease, and/or the like as described herein.

In this regard, the product 1 may be tracked and traced from arrival at the receiving entrance through any one of the freezer, the cooler, the dry goods storage area, the kitchen, and the like, and may be further tracked and traced after the product 1 is consumed as the packaging leaves the trash exit. In each case, the product related information 302 together with any sensed information from the external sensor 386, the internal sensor 384, the embedded sensor in the identifier 10, and/or the like may be obtained and forwarded to the data collection system 500. Accordingly, a detailed history of the location of the product 1, the sensed physical characteristics of the product 1, and the like may be obtained by the tracking device 300 and provided to the data collection system 500.

In some aspects, the tracking device 300 may further provide output to indicate that a particular product 1 should be used next within the facility 200. In this regard, the tracking device 300 in conjunction with the data collection system 500 may determine that a particular one of the product 1 is oldest and should be utilized next within the facility 200. This aspect may ensure an efficient usage of the product 1. Likewise, the tracking device may provide an indication that a particular one of the product 1 has expired and should be disposed of.

Figure 6:
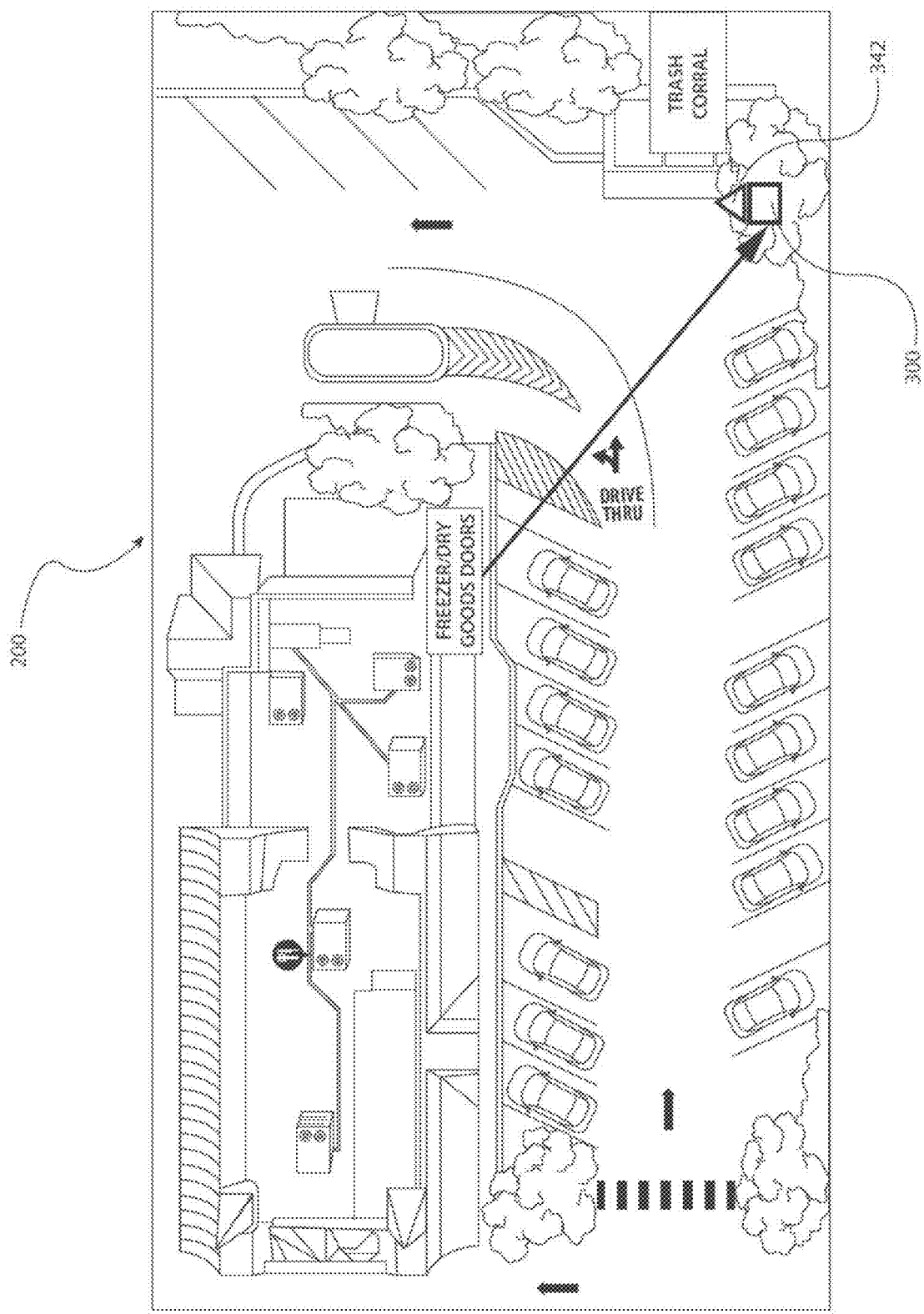
FIG. 6 illustrates the system in a particular implementation of a facility with tracking devices according to the principles of the disclosure.

FIG. 6 illustrates the system in a particular implementation of a facility with tracking devices according to the principles of the disclosure.

In particular, FIG. 6 shows the facility 200 of FIG. 5 together with an exterior view showing the trash corral. The trash corral may include a tracking device 300 together with an antenna 342. In this regard, as an employee leaves the trash exit or leaves the freezer/dry goods doors, and places the packaging with the identifier 10 into the trash corral, the tracking device 300 may track this action and update the data collection system 500 to indicate the completed consumption of the product 1.

In other aspects, a facility 200 may be a farm, a fishing boat, a slaughterhouse, and/or the like. In one aspect, when the facility 200 is a farm, the product related information 302 captured by the tracking device 300 (either manually or automatically) may include one or more of a seed type, a plant type, animal type (chicken, pork, beef), water source, feed source, farm location, types of herbicides used, types fertilizers used, organic certification, nonorganic, harvesting information (who, what, when, where, and how), veterinarian information, animal medications (type, dosage, date and time, and the like), shipping information, and the like. Accordingly, a detailed history of the location of the product 1, the sensed physical characteristics of the product 1, and the like while being planted, farmed, harvested, shipped, and the like may be obtained by the tracking device 300 and provided to the data collection system 500.

In one aspect, when the facility 200 is a fishing boat, the product related information 302 captured by the tracking device 300 (either manually or automatically) may include one or more of a fish type, fishing location, fisherman identification, boat information, as well as the other product related information 302 consistent with the disclosure (i.e., temperature), and/or the like. Accordingly, a detailed history of the location of the product 1, the sensed physical characteristics of the product 1, and the like related to fishing may be obtained by the tracking device 300 and provided to the data collection system 500. In one aspect, when the facility 200 is a fish farm, the product related information 302 captured by the tracking device 300 (either manually or automatically) may include fish type, water source, feed source, farm location, as well as the other product related information 302 consistent with the disclosure (i.e., temperature), and the like.

In one aspect, when the facility 200 is a shipping service or carrier, the product related information 302 captured by the tracking device 300 (either manually or automatically) may include one or more of a carrier identification, a vehicle type, a vehicle identification, a driver identification, a shipping date and time, a delivery date and time, time in transit moving, time in transit idling, as well as the other product related information 302 consistent with the disclosure (i.e., temperature), and/or the like. Accordingly, a detailed history of the location of the product 1, the sensed physical characteristics of the product 1, and the like related to shipping may be obtained by the tracking device 300 and provided to the data collection system 500.

Figure 7:
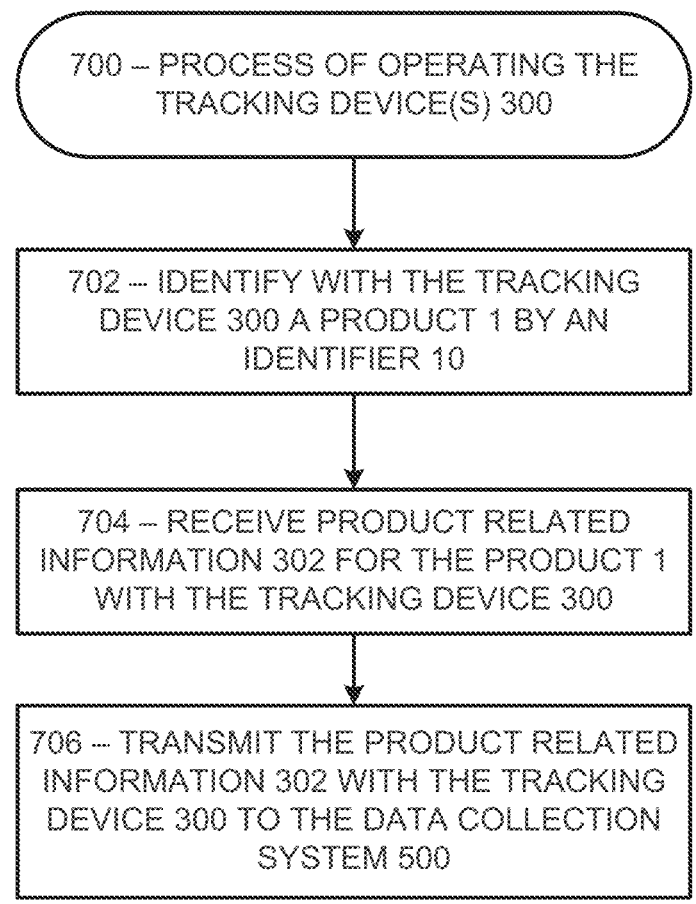
FIG. 7 illustrates a process of operating tracking devices according to principles of the disclosure.

FIG. 7 illustrates a process of operating data collection devices according to principles of the disclosure.

In particular, FIG. 7 illustrates a process 700 of operating the tracking devices 300. In one aspect, the process 700 may be implemented by each of the tracking devices 300. In particular, in one aspect, the tracking device 300 may implement the tracking application 352, that at least in part implements the process 700. In some aspects, the process 700 may utilize API functionality in response to the data collection system 500 as described herein. The following description of the process 700 provides a high-level implementation. However, with reference to the remaining disclosure, the process 700 may be implemented with much greater functionality.

As shown in FIG. 7, the process 700 may include, as illustrated in box 702, identifying with the tracking device 300 a product 1 by an identifier 10. In this regard, the identification may include machine readable codes as well as manual entry of the identifier 10 of the product 1 by the tracking device 300. In one aspect, the identifier 10 may be a machine-readable identifier that may include a radiofrequency identification (RFID) device, a barcode, a QR code, a Data Matrix (DM) code, and/or the like. In one aspect, the identifier 10 may be an alphanumeric code that may be manually input to the tracking device 300. In one aspect, the identifier 10 implemented as an RFID may be assigned and physically attached to the product 1. In one aspect, an RFID printer may print the identifier 10 implemented as an RFID and the identifier 10 may be assigned and physically attached to the product 1.

With further reference to FIG. 7, the process 700 may include, as illustrated in box 704, receiving product related information 302 for the product 1 with the tracking device 300. In this regard, the product related information 302 may include input from the internal sensor 384, the external sensor 386, as well as manual entry of the product related information 302 into the tracking device 300. In one aspect, the sensor input may include input from any one or more of an accelerometer, gyroscope, altitude sensor, temperature sensor, proximity sensor, odor sensor, IR sensor (infrared sensor), pressure sensor, light sensor, ultrasonic sensor, smoke sensor, gas sensor, alcohol sensor, touch sensor, color sensor, humidity sensor, tilt sensor, flow sensor, level sensor, motion sensor, and/or the like. In other aspects, the identifier 10 may include or connect to a number of sensors, consistent with one or more of the sensors noted above, to detect a physical characteristic of the product 1.

As further shown in FIG. 7, the process 700 may include, as illustrated in box 706, transmitting the product related information 302 to the data collection system 500 with the tracking device 300 over at least a network 400. In this regard, the tracking device 300 may include a transceiver 320 and the like. The tracking device 300 may provide radio and signal processing as needed to access the network 400, and/or the like for services over a communication channel as defined herein. In one aspect, the product related information 302 may be encrypted as described herein.

In other aspects, consistent with the disclosure, the process 700 may include operation of one or more of the camera device 326, the RFID reader 340, the location determination device 388, the audio input/output device 322, the one or more antennas 342, and the like components as disclosed herein. In some aspects, these components may provide additional information forming part of the product related information 302.

Figure 8:
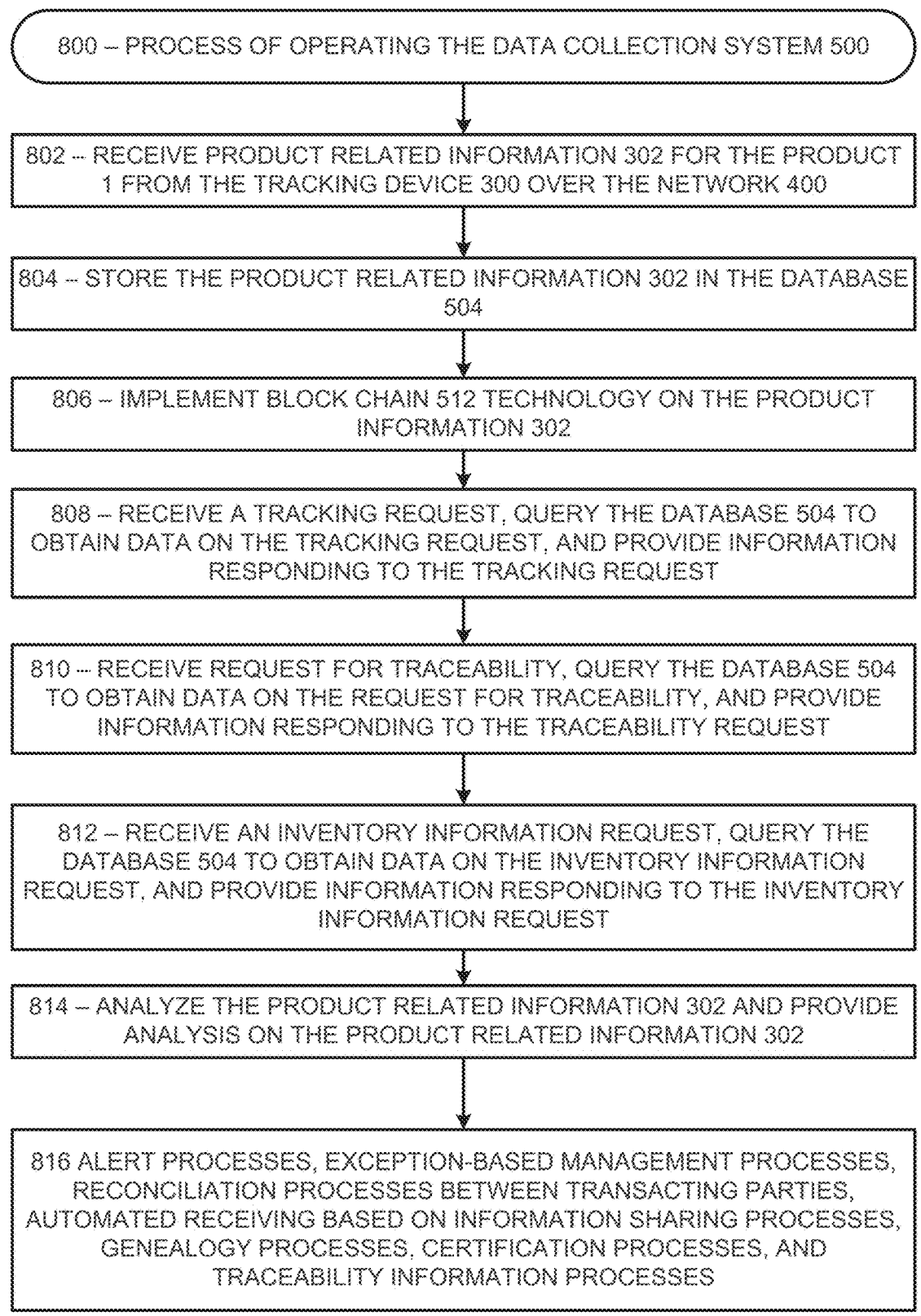
FIG. 8 illustrates a process of operating a data collection system according to principles of the disclosure.

FIG. 8 illustrates a process of operating a data collection system according to principles of the disclosure.

In particular, FIG. 8 illustrates a process 800 of operating the data collection system 500. The process 800 may be implemented, at least in part, by the data collection system 500. In some aspects, the process 800 may utilize API functionality as described herein. The following description of the process 800 provides a high-level implementation. However, with reference to the remaining disclosure, the process 800 may be implemented with much greater functionality.

As shown in FIG. 8, the process 800 may include, as illustrated in box 802, receiving product related information 302 for the product 1 from the tracking devices 300 over the network 400. In this regard, the product related information 302 may include input from the internal sensor 384, the external sensor 386, as well as manual entry of the product related information 302 into the tracking device 300. In one aspect, the sensor input may include input from any one or more of an accelerometer, gyroscope, altitude sensor, temperature sensor, proximity sensor, odor sensor, IR sensor (infrared sensor), pressure sensor, light sensor, ultrasonic sensor, smoke sensor, gas sensor, alcohol sensor, touch sensor, color sensor, humidity sensor, tilt sensor, flow sensor, level sensor, motion sensor, and/or the like. In other aspects, the identifier 10 may include or connect to a number of sensors, consistent with one or more of the sensors noted above, to detect a physical characteristic of the product 1.

With further reference to FIG. 8, the process 800 may include, as illustrated in box 804, storing the product related information 302 in the database 504.

As further shown in FIG. 8, the process 800 may include, as illustrated in box 806, implementing blockchain 512 technology on the product related information 302. In some aspects, a resulting blockchain 512 may form a ledger that may not be easily modified, changed, and the like to ensure a higher level of security and data confidence.

As further shown in FIG. 8, the process 800 may include, as illustrated in box 808, receiving a tracking request, querying the database 504 to obtain data on the tracking request, and providing information responding to the tracking request. In this regard, the query to the data collection system 500 may include a query for tracking a particular product 1 and the data collection system 500 in conjunction with the database 504 may obtain and transmit the response. In particular, the tracking functionality query can be based on the particular product 1, the particular facility 200 (farm, distribution center, restaurant, and/or the like), by case number, by lot number, by batch number, by item number, and/or the like.

With further reference to FIG. 8, the process 800 may include, as illustrated in box 810, receiving request for traceability, querying the database 504 to obtain data on the request for traceability, and providing information responding to the request traceability. In this regard, the query to the data collection system 500 may include a query for tracing a particular product 1 and the data collection system 500 in conjunction with the database 504 may obtain and transmit the response. In particular, the traceability functionality query can be based on the particular product 1, the particular facility 200 (farm, distribution center, restaurant, and/or the like), by case number, by lot number, by batch number, by item number, and/or the like.

As further shown in FIG. 8, the process 800 may include, as illustrated in box 812, receiving an inventory information request, querying the database 504 to obtain data on the inventory information request, and providing information responding to the inventory information request. In particular aspects, the data collection system 500 in response to a query may be configured to provide inventory determination, replacement determination, supply chain determination, a real-time perpetual inventory, and the like (inventory related information) based on the above noted captured information that includes the product related information 302 obtained from the tracking devices 300 in any one or more of the facilities 200. In this regard, the query to the data collection system 500 may include a query for the inventory related information and the data collection system 500 in conjunction with the database 504 may obtain and transmit the response to a computer. In one aspect, the tracking devices 300 in conjunction with the data collection system 500 may automate inbound inventory determination by detecting the product 1 when received in the facility 200.

In one aspect, the real-time perpetual inventory may include: records balance of inventory after every receipt and issue of inventory, calculated as follows: Calculation method: Closing Inventory (real time balance)=Opening balance+Receipts—Issues; Opening Inventory: Current actual inventory for the first period, that thereafter will be carried forward from prior period closing inventory balance. In some aspects, the pre-existing inventory may not have any identifier 10, and may not have any opening inventory balance; Receipts: Inventory received inside the facility 200. In one aspect, this can be either shipments from another facility 200 based on a purchase order, or a transfer from another facility 200. In this regard, the data collection system 500 may only capture receipts with the identifier 10 received from a particular one of the facilities 200; and Finally, Issue/Consumption: Consumption will be recorded when the product 1 is consumed ('Case with RFID Tag' is removed through the exit door or is present in a trash area).

With further reference to FIG. 8, the process 800 may include, as illustrated in box 814, analyzing the product related information 302 and providing analysis on the product related information 302. In particular aspects, the data collection system 500 may be configured for pathogen/disease determination from captured images obtained from the tracking device 300. In this regard, the captured images obtained from the tracking device 300 together with the product related information 302 may be analyzed by the data collection system 500 for determining indications of a pathogen, a disease, and/or the like.

With further reference to FIG. 8, the process 800 may include, as illustrated in box 816, alert processes, exception-based management processes, reconciliation processes between transacting parties, automated receiving based on information sharing processes, genealogy processes, certification processes, and traceability information processes. In this regard, the system 100 may be configured and implemented with algorithms to leverage machine learning, business rules, and artificial intelligence to proactively drive actionable insights. The system 100 may be configured and implemented to provide exception-based insights for making decisions. In this regard, the system 100 may be configured to be non-passive.

As described herein, the system 100 may be implemented such that data is chained, delivering shared value, enabling trusted, immutable transactions, and the like. Moreover, the system 100 may implement an AI model to improve inventory accuracy, may be device agnostic, may manage & deploy at scale, may implement an open source foundation, may support GS1 standards, may be API based, may be configured to provide secure & permissioned operations, and/or the like as described herein.

As a particular example, the product 1 may be fresh beef. The product 1 may be received in a manufacturing facility. The manufacturing facility defining one of the plurality of facilities. While at the manufacturing facility the fresh beef may be formed and cased. The cased fresh beef may be loaded onto a truck. The truck defining another facility. The cased fresh beef may be delivered to and received in a distribution center. The distribution center defining another facility. The cased fresh beef may be loaded onto a second truck. The second truck defining another facility. The cased fresh beef may be delivered to and received in a restaurant. The restaurant defining another facility. At the restaurant, the fresh beef may be cooked and consumed. The packaging for the case of fresh beef may be placed into a trash corral. In further aspects, the product 1 may be likewise tracked from farm to slaughterhouse. Each defining a facility. For each of the above noted facilities, the tracking device 300 may track the product 1 that is fresh beef. The product 1 is tracked through each of the facilities and finally tracked as being placed in the trash corral. Moreover, the product related information for the fresh beef may be transmitted to the data collection system 500 through each of the facilities. This particular product and these particular facilities are merely exemplary, and any type of product and any type of facility may be implemented consistent with the disclosure.

Accordingly, the disclosure has set forth a data collection system 500 and a tracking device 300 that provides increased efficiency, information, proficiency, and the like for capturing and maintaining the product related information 302 and the like for the product 1 throughout the various facilities 200. The data collection system 500 ensures implementation of the tracking devices 300. Moreover, the data collection system 500 and the tracking devices 300 as set forth in the disclosure provide detailed information on a product from its source to a final destination. Additionally, the data collection system 500 and the tracking devices 300 as set forth in the disclosure provide detailed information on a product from its source to a final destination from a single platform having a greater level of accuracy. Moreover, the data collection system 500 and the tracking devices 300 as set forth in the disclosure provide detailed information on a product from its source to a final destination having a greater speed of access to the detailed information.

EXAMPLES

Example 1

A system configured to track product and capture product related information comprising: a network interface configured to receive product related information over a network from a plurality of tracking devices located at a plurality of facilities; a database configured to store the product related information from the plurality of tracking devices located at the plurality of facilities; a processor configured to be responsive to and control at least the database and the network interface; and the processor and the database being further configured to implement blockchain technology with respect to the product related information to generate a blockchain ledger of the product related information, wherein the product related information comprises a location of a product, an identification of the product, and at least one of the following: a temperature of the product and a temperature of an environment of the product; and wherein the identification of the product is based in part on a machine-readable code located with the product, the machine-readable code comprising the identification of the product and the machine-readable code being implemented with at least one of the following: a radio frequency identification (RFID) device, a barcode, a QR (Quick Response) code, and a data matrix (DM) code.

Example 2

The system of any one or more of the examples described herein wherein: the processor is further configured to receive an information request for the product; the processor is further configured to analyze the database including the blockchain ledger to determine requested information in response to the information request for the product; and the processor is further configured to transmit the requested information to a computer, wherein the requested information comprises information on a particular one of the product, a particular one of the facilities, a case number of the product, a lot number of the product, a batch number of the product, and an item number of the product; and wherein the information request comprises at least one of the following: a tracking request and a traceability request.

Example 3

The system of any one or more of the examples described herein wherein: the processor is further configured to receive an inventory request for the product; the processor is further configured to analyze the database including the blockchain ledger to determine inventory information in response to the inventory request for the product; and the processor is further configured to transmit the inventory information to a computer, wherein the inventory information comprises at least one of the following: an inventory determination, a replacement determination, a supply chain determination, consumption metrics, inventory counts, a gross inventory, and a forecasted inventory.

Example 4

The system of any one or more of the examples described herein wherein: the product related information further comprises an image captured by a camera device implemented by one of the plurality of tracking devices; and the product related information further comprises the image captured by the camera device implemented by one of the plurality of tracking devices.

Example 5

The system of any one or more of the examples described herein wherein: the processor is further configured to analyze the image captured by the camera device implemented by one of the plurality of tracking devices to determine whether the product has indications of at least one of the following: a disease and a pathogen.

Example 6

The system of any one or more of the examples described herein further comprising the plurality of tracking devices, each of the plurality of tracking devices comprising: a machine-readable code reader configured to read a machine-readable code located with a product, the machine-readable code comprising an identification of the product and the machine-readable code being implemented with at least one of the following: a radio frequency identification (RFID) device, a barcode, a QR (Quick Response) code, and a data matrix (DM) code; at least one sensor configured to sense a physical characteristic of the product including at least one of the following: a temperature of the product and a temperature of an environment of the product; a detection unit configured to receive information from the sensor; a device processor configured to implement and control the detection unit and the machine-readable code reader; and a transceiver configured to transmit product related information over the network to the processor, the product related information comprising the location of the product, the identification of the product, and at least one of the following: the temperature of the product and the temperature of an environment of the product.

Example 7

A device configured to track product and capture product related information comprising: a machine-readable code reader configured to read a machine-readable code located with a product, the machine-readable code comprising an identification of the product and the machine-readable code being implemented with at least one of the following: a radio frequency identification (RFID) device, a barcode, a QR (Quick Response) code, and a data matrix (DM) code; at least one sensor configured to sense a physical characteristic of the product including at least one of the following: a temperature of the product and a temperature of an environment of the product; a detection unit configured to receive information from the sensor; a processor configured to implement and control the detection unit and the machine-readable code reader; and a transceiver configured to transmit product related information over a network to a data collection system, the product related information comprising a location of the product, the identification of the product, and at least one of the following: the temperature of the product and the temperature of an environment of the product.

Example 8

The device of any one or more of the examples described herein wherein: the machine-readable code reader comprises a radio frequency identification reader device; and the machine-readable code comprises the radio frequency identification (RFID) device.

Example 9

The device of any one or more of the examples described herein further comprising: a plurality of radio frequency antennas connected to the machine-readable code reader, the plurality of the radio frequency antennas arranged in different locations of a facility; and the plurality of the radio frequency antennas configured to receive the identification of the product in different locations of the facility, wherein the sensor comprises a plurality of sensors; and wherein the detection unit is further configured to receive information from the plurality of sensors.

Example 10

The device of any one or more of the examples described herein further comprising: a camera device configured to capture an image of at least one of the following: the product, an environment where the product is located, and the machine-readable code, wherein the product related information further comprises the image captured by the camera device; and wherein the transceiver is configured to transmit over the network the product related information to the data collection system that comprises the image captured by the camera device.

Example 11

A process of operating a system configured to track product and capture product related information comprising:

receiving product related information over a network with a network interface from a plurality of tracking devices located at a plurality of facilities; storing the product related information in a database from the plurality of tracking devices located at the plurality of facilities; responding to and controlling at least the database and the network interface with a processor; and implementing blockchain technology with respect to the product related information and generating a blockchain ledger of the product related information with the processor and the database, wherein the product related information comprises a location of a product, an identification of the product, and at least one of the following: a temperature of the product and a temperature of an environment of the product; and wherein the identification of the product is based in part on a machine-readable code located with the product, the machine-readable code comprising the identification of the product and the machine-readable code being implemented with at least one of the following: a radio frequency identification (RFID) device, a barcode, a QR (Quick Response) code, and a data matrix (DM) code.

Example 12

The process of any one or more of the examples described herein wherein: receiving an information request for the product with the processor; analyzing the database including the blockchain ledger and determining requested information in response to the information request for the product with the processor; and transmitting the requested information to a computer with the processor, wherein the requested information comprises information on a particular one of the product, a particular one of the facilities, a case number of the product, a lot number of the product, a batch number of the product, and an item number of the product; and wherein the information request comprises at least one of the following: a tracking request and a traceability request.

Example 13

The process of any one or more of the examples described herein wherein: receiving an inventory request for the product with the processor; analyzing the database including the blockchain ledger and determining inventory information in response to the inventory request for the product with the processor; and transmitting the inventory information to a computer with the processor, wherein the inventory information comprises at least one of the following: an inventory determination, a replacement determination, a supply chain determination, consumption metrics, inventory counts, a gross inventory, a shelf life determination, inventory determinations based on smart contracts, and a forecasted inventory.

Example 14

The process of any one or more of the examples described herein wherein: the product related information further comprises an image captured by a camera device implemented by one of the plurality of tracking devices; and the product related information further comprises the image captured by the camera device implemented by one of the plurality of tracking devices.

Example 15

The process of any one or more of the examples described herein wherein: the processor is further configured to analyze the image captured by the camera device implemented by one of the plurality of tracking devices to determine whether the product has indications of at least one of the following: a disease and a pathogen.

Example 16

The process of any one or more of the examples described herein further comprising implementing the plurality of tracking devices, the process further comprising: reading a machine-readable code located with a product with a machine-readable code reader, the machine-readable code comprising an identification of the product and the machine-readable code being implemented with at least one of the following: a radio frequency identification (RFID) device, a barcode, a QR (Quick Response) code, and a data matrix (DM) code; sensing a physical characteristic of the product with at least one sensor including at least one of the following: a temperature of the product and a temperature of an environment of the product; receiving information from the sensor with a detection unit; implementing and controlling the detection unit and the machine-readable code reader with a device processor; and transmitting product related information over a network to the processor with a transceiver, the product related information comprising a location of the product, the identification of the product, and at least one of the following: the temperature of the product and the temperature of an environment of the product.

Example 17

A process of operating a device configured to track product and capture product related information comprising: reading a machine-readable code located with a product with a machine-readable code reader, the machine-readable code comprising an identification of the product and the machine-readable code being implemented with at least one of the following: a radio frequency identification (RFID) device, a barcode, a QR (Quick Response) code, and a data matrix (DM) code; sensing a physical characteristic of the product with at least one sensor including at least one of the following: a temperature of the product and a temperature of an environment of the product; receiving information from the sensor with a detection unit; implementing and controlling the detection unit and the machine-readable code reader with a processor; and transmitting product related information over a network to a data collection system with a transceiver, the product related information comprising a location of the product, the identification of the product, and at least one of the following: the temperature of the product and the temperature of an environment of the product.

Example 18

The process of any one or more of the examples described herein wherein: the machine-readable code reader comprises a radio frequency identification reader device; and the machine-readable code comprises the radio frequency identification (RFID) device.

Example 19

The process of any one or more of the examples described herein further comprising: a plurality of radio frequency antennas connected to the machine-readable code reader, the plurality of the radio frequency antennas arranged in different locations of a facility; and the plurality of the radio frequency antennas configured to receive the identification of the product in different locations of the facility, wherein the sensor comprises a plurality of sensors; and wherein the detection unit is further configured to receive information from the plurality of sensors.

Example 20

The process of any one or more of the examples described herein further comprising: a camera device configured to capture an image of at least one of the following: the product, an environment where the product is located, and the machine-readable code, wherein the product related information further comprises the image captured by the camera device; and wherein the transceiver is configured to transmit over the network the product related information to the data collection system that comprises the image captured by the camera device.

One or more of the networks may be implemented as a wireless network and may include a radio access network (RAN). The RAN may be implemented as part of a mobile telecommunication system of the wireless network. The RAN may implement a radio access technology. The RAN may reside between the tracking devices 300 and the data collection system 500 and provide a connection with a core network (CN).

Each of the plurality of wireless networks may include the home subscriber server (HSS), or user profile server function (UPSF). The HSS may be a master user database that supports IP Multimedia Core Network Subsystem (IMS) network entities. It may contain the subscription-related information (subscriber profiles), performs authentication and authorization of the user, and can provide information about the subscriber's location and IP information. In other aspects, the wireless networks may be implemented without the home subscriber server (HSS).

In alternative or additional aspects, the wireless network may include a base transceiver station (BTS), a base station controller (BSC), and a mobile switching center (MSC) overseen by a network operator. Other types of wireless networks utilizing a communication channel as defined herein are contemplated as well. The wireless network may communicate with the tracking device 300 and/or the data collection system 500 over a communication channel as defined herein.

Reference in this specification to "one aspect," "an aspect," "other aspects," "one or more aspects" or the like means that a particular feature, structure, or characteristic described in connection with the aspect is included in at least one aspect of the disclosure. The appearances of, for example, the phrase "in one aspect" in various places in the specification are not necessarily all referring to the same aspect, nor are separate or alternative aspects mutually exclusive of other aspects. Moreover, various features are described which may be exhibited by some aspects and not by others. Similarly, various requirements are described which may be requirements for some aspects but not other aspects.

Aspects of the disclosure may include communication channels that may be any type of wired or wireless electronic communications network, such as, e.g., a wired/wireless local area network (LAN), a wired/wireless personal area network (PAN), a wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, Near field communication (NFC), a cellular telephone network, a Personal Communications Service (PCS), using known protocols such as the Global System for Mobile Communications (GSM), CDMA (Code-Division Multiple Access), GSM/EDGE and UMTS/HSPA network technologies, Long Term Evolution (LTE), 5G (5th generation mobile networks or 5th generation wireless systems), WiMAX, HSPA+, W-CDMA (Wideband Code-Division Multiple Access), CDMA2000 (also known as C2K or IMT Multi-Carrier (IMT-MC)), Wireless Fidelity (Wi-Fi), Bluetooth, and/or the like, and/or a combination of two or more thereof. The NFC standards cover communications protocols and data exchange formats, and are based on existing radio-frequency identification (RFID) standards including ISO/IEC 14443 and FeliCa. The standards include ISO/IEC 18092[3] and those defined by the NFC Forum.

Aspects of the disclosure may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

Aspects of the disclosure may be web-based. For example, a server may operate a web application in conjunction with a database. The web application may be hosted in a browser-controlled environment (e.g., a Java applet and/or the like), coded in a browser-supported language (e.g., JavaScript combined with a browser-rendered markup language (e.g., Hyper Text Markup Language (HTML) and/or the like)) and/or the like such that any computer running a common web browser (e.g., Internet Explorer™, Firefox™, Chrome™, Safari™ and/or the like) may render the application executable. A web-based service may be more beneficial due to the ubiquity of web browsers and the convenience of using a web browser as a client (i.e., thin client). Further, with inherent support for cross-platform compatibility, the web application may be maintained and updated without distributing and installing software on each.

Aspects of the disclosure may be implemented in any type of mobile smartphones that are operated by any type of advanced mobile data processing and communication operating system, such as, e.g., an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system and/or the like.

Further in accordance with various aspects of the disclosure, the methods described herein are intended for operation with dedicated hardware implementations including, but not limited to, PCs, PDAs, semiconductors, application specific integrated circuits (ASIC), programmable logic arrays, cloud computing devices, processors, microprocessors, servers, and other hardware devices constructed to implement the methods described herein.

It should also be noted that the software implementations of the disclosure as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the disclosure is considered to include a tangible storage medium or distribution medium, as listed herein and including art-recognized equivalents and successor media, in which the software implementations herein are stored. In one aspect, the software may be implemented as a non-transitory computer program product for execution on dedicated hardware implementations as defined herein.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

According to an example, the global navigation satellite system (GNSS) may include a device and/or system that may estimate its location based, at least in part, on signals received from space vehicles (SVs). In particular, such a device and/or system may obtain "pseudorange" measurements including approximations of distances between associated SVs and a navigation satellite receiver. In a particular example, such a pseudorange may be determined at a receiver that is capable of processing signals from one or more SVs as part of a Satellite Positioning System (SPS). Such an SPS may comprise, for example, a Global Positioning System (GPS), Galileo, Glonass, to name a few, or any SPS developed in the future. To determine its location, a satellite navigation receiver may obtain pseudorange measurements to three or more satellites as well as their positions at time of transmitting. Knowing the SV orbital parameters, these positions can be calculated for any point in time. A pseudorange measurement may then be determined based, at least in part, on the time a signal travels from an SV to the receiver, multiplied by the speed of light. While techniques described herein may be provided as implementations of location determination in GPS and/or Galileo types of SPS as specific illustrations according to particular examples, it should be understood that these techniques may also apply to other types of SPS, and that claimed subject matter is not limited in this respect.

The application described in the disclosure may be implemented to execute on an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system and/or the like. The application may be displayed as an icon. The application may have been downloaded from the Internet, pre-installed, and/or the like. In some aspects, the application may be obtained from Google Play™, Android Market™, Apple Store™, and/or the like digital distribution source. The application may be written in conjunction with the software developers kit (SDK) associated with an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system and/or the like.

Aspects of the disclosure may include a server executing an instance of an application or software configured to accept requests from a client and giving responses accordingly. The server may run on any computer including dedicated computers. The computer may include at least one processing element, typically a central processing unit (CPU), and some form of memory. The processing element may carry out arithmetic and logic operations, and a sequencing and control unit may change the order of operations in response to stored information. The server may include peripheral devices that may allow information to be retrieved from an external source, and the result of operations saved and retrieved. The server may operate within a client-server architecture. The server may perform some tasks on behalf of clients. The clients may connect to the server through the network on a communication channel as defined herein. The server may use memory with error detection and correction, redundant disks, redundant power supplies and so on.

As used herein interactive voice response (IVR) is a technology that allows a computer to interact with humans through the use of voice and DTMF tones input via keypad. In telecommunications, IVR allows customers to interact with a company's host system via a telephone keypad or by voice recognition, after which they can service their own inquiries by following the IVR dialogue. IVR systems can respond with prerecorded or dynamically generated audio to further direct users on how to proceed. IVR applications can be used to control almost any function where the interface can be broken down into a series of simple interactions. IVR systems deployed in the network are sized to handle large call volumes.

Voice recognition software may be utilized in various aspects of the systems and methods. Users may be able to vocalize, rather than utilizing other input processes. For example, the voice recognition software may be configured for generating text from voice input from a microphone or other voice input. A speech signal processor may convert speech signals into digital data that can be processed by the processor. The processor may perform several distinct functions, including serving as the speech event analyzer, the dictation event subsystem, the text event subsystem, and the executor of the application program. The speech signal processor may generate speech event data and transmit this data to the processor to be processed first by the speech event analyzer. The speech event analyzer may generate a list or set of possible candidates among the system recordings that represent or match the voice input processed by the speech signal processor. The speech event analyzer may transmit the candidate sets to a dictation event subsystem. The dictation event subsystem may analyze the candidate sets and choose the best match candidate with the highest degree of similarity. This candidate is then considered the correct translation, and the dictation event subsystem forwards the translation to the text event subsystem which in turn inputs the translated text into the device.

The term text message or SMS refers to "short message service" which is a text messaging service component of phone, web, or mobile communication systems. It uses standardized communications protocols to allow fixed line or mobile phone devices to exchange short text messages. SMS was originally designed as part of GSM, but is now available on a wide range of networks, including 3G, 4G, LTE, 5G networks or networks associated with the communication channel as defined herein. In other aspects, text message may include Multimedia Messaging Service (MMS), which is a standard way to send messages that include multimedia content to and from mobile phones. It extends the core SMS (Short Message Service) capability that allowed exchange of text messages only up to 160 characters in length. While the most popular use is to send photographs from camera-equipped handsets, it is also used as a method of delivering news and entertainment content including videos, pictures, text pages and ringtones. MMS can be used within the context of the present invention for UICC activation message delivery. Of note is that MMS messages are delivered in a completely different way from SMS. The first step is for the sending device to encode the multimedia content in a fashion similar to sending a MIME e-mail (MIME content formats are defined in the MMS Message Encapsulation specification). The message is then forwarded to the carrier's MMS store and forward server, known as the MMSC (Multimedia Messaging Service Centre). If the receiver is on another carrier, the relay forwards the message to the recipient's carrier using the Internet.

The term voice or voice calls as utilized herein may include voice calls defined by 3GPP (3rd Generation Partnership Project) with Voice Call Continuity (VCC) specifications in order to describe how a voice call can be persisted, as a mobile phone moves between circuit switched and packet switched radio domains (3GPP TS 23.206).

The term data as utilized herein includes mobile broadband or wireless Internet access delivered through mobile phone towers over a communication channel as defined herein to computers, mobile phones, wireless devices, and other digital devices as defined herein using portable modems. Some mobile services allow more than one device to be connected to the Internet using a single cellular connection using a process called tethering.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

What is claimed is:

1. A system configured to track product and capture product related information comprising:
   a network interface configured to receive product related information over a network from a plurality of tracking devices located at a plurality of facilities utilizing at least one of the following: a micro service transformation layer where multiple data sources converge to configure, format, and normalize data to a common language and a network of interfaces and APIs ingesting data to a blockchain platform comprising replicated instances of a database;
   the database configured to store the product related information received by the network interface from the plurality of tracking devices located at the plurality of facilities;
   a processor configured to be responsive to and control at least the database and the network interface; and
   the processor and the database being further configured to implement blockchain technology with respect to the product related information received from the plurality of tracking devices to generate a blockchain ledger of the product related information,
   wherein the product related information provided by the plurality of tracking devices comprises a location of a product, an identification of the product, and at least one of the following: a temperature of the product, remaining product shelf life, identifying characteristics, and a temperature of an environment of the product;
   wherein the identification of the product is provided by the plurality of tracking devices and is based in part on a machine-readable code located with the product, the machine-readable code comprising the identification of the product and the machine-readable code being implemented with at least one of the following: a radio frequency identification (RFID) device, a barcode, a QR (Quick Response) code, and a data matrix (DM) code;
   wherein the network interface is configured to receive the product related information over the network from at least one of the plurality of tracking devices located in at least one of the plurality of facilities when a product arrives in the at least one of the plurality of facilities, update the database, and the processor being configured to generate and send tracking information, traceability information, inventory information, and/or issues with the product to a user;
   wherein the network interface is configured to receive the product related information over the network from at least one of the plurality of tracking devices located in the at least one of the plurality of facilities when the product is processed in the at least one of the plurality of facilities, update the database, and the processor being configured to generate and send tracking information, traceability information, inventory information, and/or issues with the product to the user;
   wherein the network interface is configured to receive the product related information over the network from at least one of the plurality of tracking devices located in the at least one of the plurality of facilities when the product departs from the at least one of the plurality of facilities, update the database, and the processor being configured to generate and send tracking information, traceability information, inventory information, and/or issues with the product to the user;
   wherein the processor is further configured to receive an information request for the product from a computer in response to the user;
   wherein the processor is further configured to analyze the database including the blockchain ledger to determine requested information in response to the information request for the product; and
   wherein the processor is further configured to transmit the requested information to the computer for the user.

2. The system of claim 1 wherein:
   wherein the requested information from the computer in response to the user comprises information on a particular one of the product, a particular one of the facilities, a case number of the product, a lot number of the product, a batch number of the product, and an item number of the product; and
   wherein the information request comprises at least one of the following: a tracking request, a product genealogy request, and a traceability request.

3. The system of claim 1 wherein:
   the network interface is configured to implement encryption functionality and decryption functionality:
   the processor is further configured to receive an inventory request for the product from a computer or a mobile device in response to a user;
   the processor is further configured to analyze the database including the blockchain ledger to determine inventory information in response to the inventory request for the product;
   the processor is further configured to transmit the inventory information to the computer or the mobile device for the user; and the inventory information comprises at least one of the following: an inventory determination, a replacement determination, a supply chain determination, consumption metrics, inventory counts, a gross inventory, and a forecasted inventory.

4. The system of claim 1 wherein:
at least one of the plurality of tracking devices is configured to implement a camera device;
the product related information further comprises an image captured by the camera device implemented by one of the plurality of tracking devices;
the network interface is configured to receive the image from one of the plurality of tracking devices; and
the product related information further comprises the image captured by the camera device implemented by one of the plurality of tracking devices.

5. The system of claim 4 wherein:
the processor is further configured to analyze the image captured by the camera device implemented by one of the plurality of tracking devices to determine whether the product has indications of at least one of the following: quality characteristics and product integrity information.

6. A process of operating a system configured to track a product and capture product related information comprising:
receiving product related information over a network with a network interface from a plurality of tracking devices located at a plurality of facilities;
storing the product related information in a database received by the network interface from the plurality of tracking devices located at the plurality of facilities;
responding to and controlling at least the database and the network interface with a processor; and
implementing blockchain technology with respect to the product related information and generating a blockchain ledger of the product related information received from the plurality of tracking devices with the processor and the database;
receiving the product related information with the network interface over the network from at least one of the plurality of tracking devices located in at least one of the plurality of facilities when a product arrives in the at least one of the plurality of facilities, updating the database, and generating and sending with the processor tracking information, traceability information, inventory information, and/or issues with the product to a user;
receiving the product related information with the network interface over the network from at least one of the plurality of tracking devices located in the at least one of the plurality of facilities when the product is processed in the at least one of the plurality of facilities, updating the database, and generating and sending with the processor tracking information, traceability information, inventory information, and/or issues with the product to the user;
receiving the product related information with the network interface over the network from at least one of the plurality of tracking devices located in the at least one of the plurality of facilities when the product departs from the at least one of the plurality of facilities, updating the database, and generating and sending with the processor tracking information, traceability information, inventory information, and/or issues with the product to the user;
receiving an information request for the product from a computer in response to the user with the processor;
analyzing the database including the blockchain ledger and determining requested information in response to the information request for the product with the processor; and
transmitting the requested information to the computer for the user with the processor,
wherein the network interface is configured to receive product related information over a network from a plurality of tracking devices located at a plurality of facilities utilizing at least one of the following: a micro service transformation layer where multiple data sources converge to configure, format, and normalize data to a common language and a network of interfaces and APIs ingesting data to a blockchain platform comprising replicated instances of a database;
wherein the product related information provided by the plurality of tracking devices comprises a location of a product, an identification of the product, and at one of the following: a temperature of the product and a temperature of an environment of the product; and
wherein the identification of the product is provided by the plurality of tracking devices and is based in part on a machine-readable code located with the product, the machine-readable code comprising the identification of the product and the machine-readable code being implemented with at least one of the following: a radio frequency identification (RFID) device, a barcode, a QR (Quick Response) code, and a data matrix (DM) code.

7. The process of claim 6 wherein:
wherein the requested information comprises information on a particular one of the product, a particular one of the facilities, a case number of the product, a lot number of the product, a batch number of the product, and an item number of the product; and
wherein the information request comprises at least one of the following: a tracking request and a traceability request.

8. The process of claim 6 wherein:
receiving an inventory request for the product from a computer in response to a user with the processor;
analyzing the database including the blockchain ledger and determining inventory information in response to the inventory request for the product with the processor; and
transmitting the inventory information to the computer for the user with the processor,
wherein the inventory information comprises at least one of the following: an inventory determination, a replacement determination, a supply chain determination, consumption metrics, inventory counts, a gross inventory, a shelf life determination, inventory determinations based on smart contracts, and a forecasted inventory.

9. The process of claim 6 wherein:
at least one of the plurality of tracking devices is configured to implement a camera device;
the product related information further comprises an image captured by the camera device implemented by one of the plurality of tracking devices; and
the product related information further comprises the image captured by the camera device implemented by one of the plurality of tracking devices.

10. The process of claim 9 wherein:
the processor is further configured to analyze the image captured by the camera device implemented by one of the plurality of tracking devices to determine whether the product has indications of at least one of the following: a disease and a pathogen.

11. The process of claim 6 further comprising implementing the plurality of tracking devices, the process further comprising:
   reading a machine-readable code located with a product with a machine-readable code reader, the machine-readable code comprising an identification of the product and the machine-readable code being implemented with at least one of the following: a radio frequency identification (RFID) device, a barcode, a QR (Quick Response) code, and a data matrix (DM) code;
   sensing a physical characteristic of the product with at least one sensor including at least one of the following: a temperature of the product and a temperature of an environment of the product;
   receiving information from the sensor with a detection unit;
   implementing and controlling the detection unit and the machine-readable code reader with a device processor; and
   transmitting product related information over a network to the processor with a transceiver, the product related information comprising a location of the product, the identification of the product, and at least one of the following: the temperature of the product and the temperature of an environment of the product.

12. The system of claim 1 wherein:
   the product related information further comprises an image captured by a camera device implemented by one of the plurality of tracking devices;
   the plurality of tracking devices being configured to capture the image and the image comprises an image of the product and/or an image of a food preparation surface
   the network interface is configured to receive the image from one of the plurality of tracking devices being; and
   the product related information further comprises the image captured by the camera device implemented by one of the plurality of tracking devices.

13. The system of claim 12 wherein:
   the processor is further configured to analyze the image captured by the camera device implemented by one of the plurality of tracking devices to determine whether the image has indications of at least one of the following: product quality characteristics, product integrity information, a pathogen, and/or a disease.

14. The system of claim 1 wherein at least one of the plurality of tracking devices is implemented as an Internet of things (IoT) implemented in at least one of the plurality of facilities.

15. The process of claim 9 further comprising analyzing with the processor the image captured by the camera device implemented by one of the plurality of tracking devices to determine whether the image has indications of at least one of the following: product quality characteristics, product integrity information, a pathogen, and/or a disease.

* * * * *